(12) United States Patent
Weber et al.

(10) Patent No.: US 7,244,743 B2
(45) Date of Patent: Jul. 17, 2007

(54) NON-PEPTIDIC BRS-3 AGONISTS

(75) Inventors: Dirk Weber, Munich (DE); Horst Kessler, Gorching (DE); Claudia Berger, Backnang (DE); Jochen Antel, Bad Muender (DE); Timo Heinrich, Gross-Umstadt (DE)

(73) Assignee: Solvay Pharmaceuticals GmbH, Hannover (DE)

(*) Notice: Subject to any disclaimer, the term of this patent is extended or adjusted under 35 U.S.C. 154(b) by 0 days.

(21) Appl. No.: 11/002,131

(22) Filed: Dec. 3, 2004

(65) Prior Publication Data

US 2005/0171146 A1 Aug. 4, 2005

Related U.S. Application Data

(63) Continuation of application No. PCT/EP03/05678, filed on May 30, 2003.

(30) Foreign Application Priority Data

Jun. 5, 2002 (DE) ............................... 102 24 844

(51) Int. Cl.
- A61K 31/404 (2006.01)
- A61K 31/4439 (2006.01)
- C07D 209/14 (2006.01)
- C07D 401/12 (2006.01)

(52) U.S. Cl. .................... 514/307; 514/339; 514/414; 514/419; 546/146; 546/277.4; 548/455; 548/491

(58) Field of Classification Search .................... None
See application file for complete search history.

(56) References Cited

U.S. PATENT DOCUMENTS

| | | | |
|---|---|---|---|
| 5,153,226 A | 10/1992 | Chucholowski et al. | |
| 5,200,408 A | 4/1993 | Bru-Magniez et al. | |
| 5,565,568 A | 10/1996 | Cho et al. | |
| 5,773,441 A | 6/1998 | Hipskind et al. | |
| 6,194,437 B1 | 2/2001 | Horwell et al. | |
| 6,307,017 B1 | 10/2001 | Coy et al. | |
| 2002/0028799 A1 | 3/2002 | Naylor et al. | |
| 2002/0055759 A1 | 5/2002 | Shibuya | |
| 2002/0058606 A1 | 5/2002 | Gonzalez et al. | |
| 2002/0169101 A1 | 11/2002 | Gonzalez et al. | |
| 2002/0177689 A1 | 11/2002 | Benson et al. | |
| 2003/0119714 A1 | 6/2003 | Naylor et al. | |
| 2004/0023862 A1 | 2/2004 | Smart et al. | |
| 2004/0039198 A1 | 2/2004 | Bender et al. | |
| 2004/0087561 A1 | 5/2004 | Gonzalez et al. | |
| 2004/0110768 A1 | 6/2004 | Higginbottom et al. | |
| 2004/0116440 A1 | 6/2004 | Higginbottom et al. | |

FOREIGN PATENT DOCUMENTS

| | | | |
|---|---|---|---|
| EP | 0 415 413 A1 | | 3/1991 |
| WO | WO 92/02244 | * | 2/1992 |
| WO | WO 95/00542 A1 | | 1/1995 |
| WO | WO 97/06803 A1 | | 2/1997 |
| WO | WO 98/07718 A1 | | 2/1998 |
| WO | WO 98/31214 A1 | | 10/1998 |
| WO | WO 01/68120 A2 | | 9/2001 |
| WO | WO 02/40008 A2 | | 5/2002 |
| WO | WO 02/40022 A1 | | 5/2002 |
| WO | WO 02/40069 A2 | | 5/2002 |
| WO | WO 02/40468 A1 | | 5/2002 |
| WO | WO 02/40469 A1 | | 5/2002 |
| WO | WO 02/40475 A1 | | 5/2002 |

OTHER PUBLICATIONS

Weber et al., "Systemic Optimization of a Lead-Structure Identifies for a Selective Short Peptide Agonist for the Human Orphan Receptor BRS-3," J. of Peptide Science, vol. 8, pp. 461-475 (2002).*

Weber et al., "Design of Selective Peptidomimetic Agonists for the Human Orphan Receptor BRS-3#," J. Med. Chem., 46(10), pp. 1918-1930 (2003).*

Barbara Dorner, et al., "Preparation of Carboxy-Modified Peptide Fragments using Alkyoxybenzaldehyde Resins", Peptides, 1998, pp. 90 and 91, Akadémiai Kiadó, Budapest, 1999

Achim Fleischmann, et al., "Bombesin Receptors in Distinct Tissue Compartments of Human Pancreatic Diseases", Laboratory Investigation, Dec. 2000, pp. 1807-1817, vol. 80, No. 12, The United States and Canadian Academy of Pathology, Inc.

Valentin Gorbulev, et al., "Organization and Chromosomal Localization of the Gene for the Human Bombesin Receptor Subtype Expressed in Pregnant Uterus" FEBS Letters, 1994, pp. 260-264, vol. 340, Federation of European Biochemical Societies.

Samuel A. Mantey, et al., "Rational Design of a Peptide Agonist that Interacts Selectively with the Orphan Receptor, Bombesin Receptor Subtype 3*", Sep. 2000, pp. 9219-9229, JBC Papers in Press, Published Dec. 8, 2000.

Hiroko Ohki-Hamazaki, et al., "Mice Lacking Bombesin Receptor Subtype-3 Develop Metabolic Defects and Obesity", Letters to Nature, Nov. 1997, pp. 165-169, vol. 390. .

(Continued)

Primary Examiner—Kamal A. Saeed
Assistant Examiner—Andrew B. Freistein
(74) Attorney, Agent, or Firm—Crowell & Moring LLP

(57) ABSTRACT

Selectively BRS-3-agonistic compounds of formula I $$Ar^1-(CH_2)_m-A^1-A^2-N-A^3 \underset{H}{\overset{O}{\underset{\|}{C}}} \underset{H}{\overset{R^1}{\underset{|}{N}}} \underset{O}{\overset{Ar^2}{\underset{\|}{C}}} \underset{H}{\overset{R^3}{\underset{|}{N}}} (CH_2)_n-Ar^3$$

wherein $A^1$, $A^2$, $A^3$, $R^1$, $R^2$, $R^3$, $Ar^1$, $Ar^2$, $Ar^3$, m and n have the meanings given in the description, and also pharmaceutical compositions containing these compounds and a process for the preparation of compounds of Formula I are described.

11 Claims, No Drawings

OTHER PUBLICATIONS

Baodong Sun, "Presence of Receptors for Bombesin/Gastrin-Releasing Peptide and mRNA for Three Receptor Subtypes in Human Prostate Cancers", The Prostate, 2000, pp. 295-303, vol. 42, Wiley-Liss, Inc.

Dirk Weber, et al., "Design of Selective Peptidomimetric Agonists for the Human Orphan Receptor BRS-3#", Apr. 15, 2003, pp. 1918-1930, vol. 46, No. 10, American Chemical Society.

Kazuyuki Yamada, et al., "Differential Effects of Social Isolation upon Body Weight, Food Consumption, and Responsiveness to Novel and Social Environment in Bombesin Receptor Subtype-3 (BRS-3) Deficient Mice", Physiology & Behavior, 2000, pp. 555-561, vol. 68, Elsevier Science Inc.

A. Flörsheimer, et al., "Solid-Phase Synthesis of Peptides with the Highly Acid-Sensitive HMPB Linker", Peptides, 1990, pp. 131-133, ESCOM Science Publishers B.V., Published 1991.

Von Rudolf Gretler, et al., The Mass Spectral Retro-Diels-Alder-Reaction: 1,2,3,4-Tetrahydroisoquinoline and 1,2,3,4-Tetrahydronaphthalina (Tetraline) (1978).

Samuel A. Mantey, et al., Discovery of a High Affinity Radioligand for the Human Orphan Receptor, Bombesin Receptor Subtype 3, Which Demonstrates that has a Unique Pharmacology Compared with Other Mammalian Bombesin Receptors, The Journal of Biological Chemistry, Oct. 10, 1997, pp. 26062-26071, vol. 272, No. 41.

Tapas K. Pradhan, et al., "Identification of a Unique Ligand which has High Affinity for All Four Bombesin Receptor Subtypes", European Journal Of Pharmacology, 1998, pp. 275-287, vol. 343, Elsevier Science B.V., Published Nov. 14, 1997.

Dirk Weber, et al., "Systemic Optimization of a Lead-Structure Identifies for a Selective Short Peptide Agonist for the Human Orphan Receptor BRS-3", Journal of Peptide Science, 2002, pp. 461-475, vol. 8, European Peptide Society and John Wiley & Sons, Ltd.

James M. Wu, et al., "Discovery of High Affinity Bombesin Receptor Subtype 3 Agonists", Molecular Pharmacology, 1996, pp. 1355-1363, vol. 50, The American Society of Pharmacology and Experimental Therapeutics.

Kazuyuki Yamada, et al., "Hyperresponsiveness to Palatable and Aversive Taste Stimuli in Genetically Obese (Bombesin Receptor Subtype-3-Deficient) Mice", Physiology & Behavior, 1999, pp. 863-867, vol. 66, No. 5, Elsevier Science Inc., PII S0031-9384(99)00032-3.

Zahra Fathit§, et al., "BRS-3: A Novel Bombesin Receptor Subtype Selectively Expressed in Testis and Lung Carcinoma Cells", The Journal of Biological Chemistry, Mar. 15, 1993, pp. 5979-5984, vol. 268, No. 8, Published Sep. 30, 1992.

Valentin Gorbulev, et al., "Molecular Cloning of a New Bombesin Receptor Subtype Expressed in Uterus During Pregnancy", European Journal of Biochemistry, 1992, pp. 405-410, FEBS 1992.

Antonello Mai, et al., "5-Alkyl-2-(Alkylthio)-6-(2,6-Dihalophenylmethyl)-3,4-Dihydropyrimidin-4(3H)-c Novel Potent and Selective Dihydro-Alkoxy-Benzyl-Oxopyrimidine Derivative", J. Med. Chem., 1999, pp. 619-627, vol. 42, American Chemistry Society, Published Feb. 5, 1999.

Christopher J. Moody, et al., "Diels-Alder Reactivity of Pyrano[4,3-b]indol-3-ones, Indole 2,3-Quinodimethane Analogues", J. Chem. Soc., 1990, pp. 673-679.

Baodong Sun, et al., "The Presence of Receptors for Bombesin/GRP and mRNA for Three Receptor Subtypes in Human Ovarian Epithelial Cancers", Regulatory Peptides, 2000, pp. 77-84, vol. 90, Elsevier Science B.V.

K. Yamada, et al., "Role of Bombesin (BN)-like Peptides/Receptors in Emotional Behavior by Comparison of Three Strains of BN-like Peptide Receptor Knockout Mice", Molecular Psychiatry, 2002, pp. 113-117, vol. 7, Nature Publishing Group.

* cited by examiner

NON-PEPTIDIC BRS-3 AGONISTS

CROSS REFERENCE TO RELATED APPLICATIONS

This application is a continuation of international patent application No. PCT/EP03/05678, filed May 30, 2003, designating the United States of America, the entire disclosure of which is incorporated herein by reference. Priority is claimed based on Federal Republic of Germany patent application No. DE 102 24 844.3, filed Jun. 5, 2002.

BACKGROUND OF THE INVENTION

The present invention relates to novel, non-peptidic compounds which exhibit a selective agonistic action on the bombesin receptor of subtype 3 (BRS-3), and to pharmaceutical preparations containing these compounds and also processes for the preparation of these compounds.

Bombesin (Bn) is a peptide consisting of 14 amino acids which was originally isolated from amphibians. The two peptides neuromedin B (NMB) and the "gastrin-releasing peptide" (GRP) which have been identified in mammals represent structurally similar peptides. These bombesin-like peptides are the naturally endogenous ligands of the corresponding bombesin receptors, the "neuromedin B receptor" (NMB-R, BB1) and the "gastrin-releasing peptide receptor" (GRP-R, BB2). The bombesin receptors belong to the group of the G-coupled receptors with 7 transmembrane domains.

Due to the homology of its amino acid sequence, the bombesin receptor of subtype 3 (BRS-3 or BB3) is assigned to this family of bombesin receptors [cf. Fathi et al. (1993) J. Biol. Chem. 268:5979-84; cited below as "Fathi et al."]. The natural ligand of BRS-3 is hitherto unknown. The expression of BRS-3 was demonstrated in various regions of the brain [cf. Yamada et al. (1999) Physiol. Behav. 66:863-7], in secondary spermatocytes [cf. Fathi et al.], in pancreatic islet cells [cf. Fleischmann et al. (2000) Lab. Invest. 80:1807-17] and in the uterine tissue of pregnant animals [cf. Gorbulev et al. (1992) Eur. J. Biochem. 208:405-10]. Furthermore, BRS-3 was identified in different human cancer cell lines (e.g. lung [cf. Fathi et al.], breast [cf. Gorbulev et al. (1994) FEBS Lett. 340:260-4], prostate [cf. Sun et al. (2000) Prostate. 42:295-303] or ovary [cf. Sun et al. (2000) Regul. Pept. 90:77-84]).

Genetically altered mice in which the BRS-3 gene had been knocked out ("BRS-3 Knockout Mice") exhibited a clinical picture which comprised obesity, hyperphagia and also hypertension and diabetes [cf. Okhi-Hamazaki et al. (1997) Nature 390:165-9]. According to this, BRS-3 appears to be an essential participant in the regulation of glucose metabolism and lipometabolism, in maintaining the energy status and in controlling blood pressure, and also in influencing eating behaviour. It can therefore be assumed of BRS-3 agonistic compounds that they are suitable in particular for the prophylaxis and/or treatment of pathological conditions such as obesity (=adiposity), diabetes, hyperinsulinism, cardiovascular diseases, eating disorders (hyperphagia, anorexia, bulimia) and/or metabolic syndrome (=syndrome X). Syndrome X manifests itself above all by Type II diabetes mellitus and/or reduced glucose tolerance, arterial hypertension, lipometabolism disorders, obesity and also coronary heart disease.

Furthermore, it is known that the activation of BRS-3 can have a neuro-protective action [cf. WO 01/68120]. Also BRS-3 appears to be connected to taste perception [cf. Yamada et al. (1999) Physiol. Behav. 66:863-7], influencing of social behaviour [cf. Yamada et al. (2000) Physiol. Behav. 68:555-61] and certain emotional behaviors [cf. Yamada et al. (2002) Mol. Psychiatry. 7:113-7]. It can therefore likewise be assumed that BRS-3-modulatory compounds may be suitable for the prophylaxis and/or treatment of psychic clinical pictures such as depression or anxiety states, taste perception disorders and/or degenerative diseases of the central nervous system, for example Parkinson's or Alzheimer's.

Some synthetic peptidic ligands are already known which bind with a certain affinity to BRS-3 and exert an agonistic action thereon, namely the BRS-3 selective octapeptide [D-Phe$^6$, Phe$^{13}$]Bn(6-13) propylamide [cf. Wu et al. (1996) Mol. Pharmacol. 50:1355-63] and also the less-selective nonapeptide [D-Tyr$^6$, β-Ala$^{11}$, Phe$^{13}$, Nle$^{14}$]Bn(6-14) [cf. Mantey et al. (1997) J. Biol. Chem. 272:26062-71] and its derivatives [cf. Pradhan et al. (1998) J. Pharmacol. 343:275-87; Mantey et al. (2001) J. Biol. Chem. 276:9219-29].

Low-molecular, non-peptidic bombesin-analogous compounds are furthermore already known from WO 98/07718, but these are selective antagonists of the other two subtypes of the bombesin receptor family (NMB-R and GRP-R). Low-molecular, non-peptidic compounds which have a selective agonistic effect with high affinity to BRS-3 on the other hand have not been described hitherto.

SUMMARY OF THE INVENTION

It is therefore an object of the present invention to provide new, low-molecular weight, non-peptidic compounds which have a selective agonistic effect with high affinity to BRS-3.

It has now surprisingly been discovered that the low-molecular and non-peptidic novel compounds according to the invention are selective BRS-3 agonists and are thus suitable for the prophylaxis and/or treatment of clinical pictures which can be influenced beneficially by stimulating the BRS-3. Owing to their activity profile, the compounds of the invention appear to be suitable in particular for the treatment or inhibition of obesity (=adiposity), diabetes, hyperinsulinism, cardiovascular diseases, eating disorders (hyperphagia, anorexia, bulimia) and/or syndrome X.

The invention thus relates in a first aspect to novel compounds of the general formula I

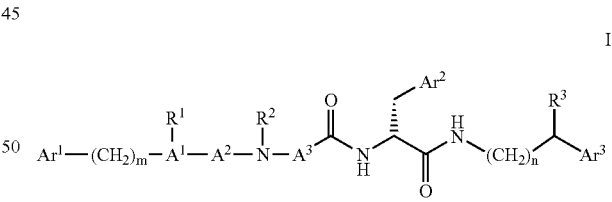

wherein
A$^1$ is CH or, if A$^2$ does not stand for a bond and at the same time A$^3$ does not stand for NH, also nitrogen,
A$^2$ is a bond, C$_{1-2}$-alkylene or, if A$^1$ stands for CH and R$^2$ stands for hydrogen, also carbonyl,
A$^3$ is methylene which is optionally substituted by C$_{1-4}$-alkyl or C$_{1-4}$-alkyl carbonylamide or, if R$^2$ is hydrogen or together with R$^1$ stands for a bond, is also NH,
R$^1$ is hydrogen or, if A$^2$ stands for carbonyl, also amino, and R$^2$ is hydrogen, or
R$^1$ and R$^2$ together form C$_{1-2}$-alkylene or, if A$^2$ is a bond, R$^1$ and R$^2$ may also together stand for a bond,
R$^3$ is hydrogen or methyl, Ar¹ is phenyl which is optionally substituted 1 to 2 times by halogen or $C_{1-4}$-alkyl or by $C_{1-2}$-alkylenedioxy bonded to two adjacent ring carbon atoms; pyridyl, furyl, indolyl or tetrahydroisoquinolyl, Ar² is furyl, benzofuranyl, thienyl, benzothiophenyl, pyrrolyl or indolyl, Ar³ is phenyl which is optionally substituted 1 to 2 times by halogen, or pyridyl, m is 0 or 1 and n is 0 or 1, and also optionally their physiologically compatible acid addition salts. In further aspects, the invention also relates to pharmaceutical preparations containing the compounds of Formula I and to a process for the preparation of such compounds.

Where substituents $C_{1-4}$-alkyl are contained in the compounds of Formula I, this may be straight-chain or branched. Where substituents contain halogen, this may be in particular fluorine, chlorine or bromine. Chlorine is preferred.

Where A³ is substituted by $C_{1-4}$-alkyl, methyl is preferred. Where A³ is substituted by $C_{1-4}$ alkyl carbonylamide, n-propylamide is preferred.

R³ preferably stands for hydrogen.

Ar¹ is preferably phenyl which is optionally substituted once by halogen; pyridyl, furyl, in particular 2-furyl, or indolyl, in particular 2-indolyl.

Ar² preferably stands for benzothiophenyl or for indolyl. Indolyl, in particular 3-indolyl, is preferred.

Ar³ preferably stands for phenyl, in particular non-substituted phenyl.

n is preferably 1.

Preferred compounds of Formula I include:

compounds of the general formula Ia

Ia wherein Ar¹ and m have the above meanings, $R^{101}$ is hydrogen or amino, R⁴ is hydrogen, $C_{1-4}$-alkyl or $C_{1-4}$-alkyl carbonylamide and $Ar^{201}$ is benzothiophenyl or indolyl;

compounds of the general formula Ib

Ib wherein R⁴, Ar¹, $Ar^{201}$ and m have the above meanings;

compounds of the general formula Ic

Ic wherein Ar¹, $Ar^{201}$ and m have the above meanings;

compounds of the general formula Id

Id wherein Ar¹, $Ar^{201}$ and m have the above meanings;

compounds of the general formula Ie

Ie wherein Ar¹, $Ar^{201}$ and m have the above meanings, and compounds of the general formula If If wherein A¹, Ar¹, $Ar^{201}$ and m have the above meanings.

The compounds of Formula I represent non-peptidic compounds, which however contain peptide bonds. The compounds of Formula I can therefore be regarded as non-natural polypeptides and be constructed partially or completely in a manner known for polypeptide synthesis, for example by conventional solid- or liquid-phase synthesis techniques with suitable amino and carboxyl building blocks, preferably sequentially. Where additionally also other organic-chemical synthesis methods are used for constructing the compounds of Formula I, known conventional organic-chemical synthesis methods may be used.

Thus the compounds of Formula I and their acid addition salts may for example be prepared in that a) for the preparation of a compound of the general formula Ig, Ig

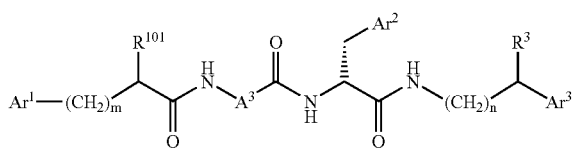

wherein $A^3$, $R^{101}$, $R^3$, $Ar^1$, $Ar^2$, $Ar^3$, m and n have the above meanings,
a compound of Formula II

II

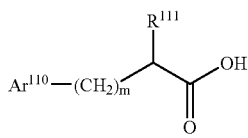

wherein m has the above meaning, $Ar^{110}$ has the meaning given above for $Ar^1$, any reactive groups being protected by protective groups, and $R^{111}$ has the meaning given above for $R^{101}$, any amino group being protected by a protective group, is reacted with
a compound of the general formula III

III

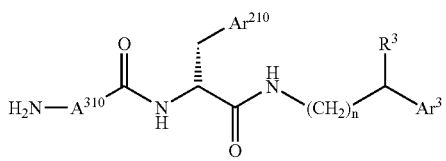

wherein $R^3$, $Ar^3$ and n have the above meanings, $Ar^{210}$ has the meaning given above for $Ar^2$, any reactive groups being protected by protective groups, and $A^{310}$ has the meaning given above for $A^3$, any reactive nitrogen atoms being protected by protective groups, or b) for the preparation of a compound of the general formula Ih Ih

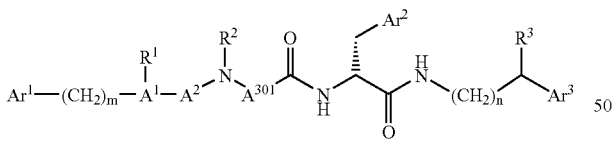

wherein $A^1$, $A^2$, $R^1$, $R^2$, $R^3$, $Ar^1$, $Ar^2$, $Ar^3$, m and n have the above meanings and $A^{301}$ has the meaning given above for $A^3$ with the exception of NH, a compound of the general formula IV

IV

wherein $A^1$, $A^2$, $Ar^{110}$ and m have the above meanings, $A^{311}$ has the meaning given above for $A^{301}$, any reactive nitrogen atoms being protected by protective groups, $R^{110}$ has the meaning given above for $R^1$, any amino groups being protected by a protective group, and $R^{201}$ has the meaning given above for $R^2$ with the exception of hydrogen, or represents an amino protective group, is reacted with a compound of the general formula V

V

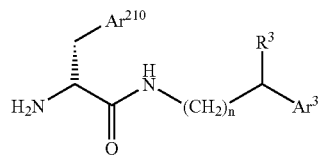

wherein $R^3$, $Ar^{210}$, $Ar^3$ and n have the above meanings, or
c) for the preparation of a compound of the general formula Ii, Ii

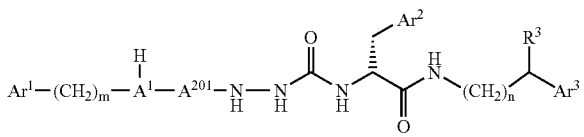

wherein $A^1$, $R^3$, $Ar^1$, $Ar^2$, $Ar^3$, m and n have the above meanings and $A^{201}$ has the meaning given above for $A^2$ with the exception of carbonyl, a compound of Formula V is reacted with a carbonyl-group synthesis equivalent and with a compound of the general formula VI

VI

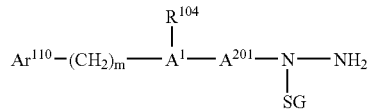

wherein $A^1$, $A^{201}$, $Ar^{110}$ and m have the above meanings, $R^{104}$ stands for hydrogen or, if $A^1$ is nitrogen, may also stand for a nitrogen protective group, and SG stands for a protective group suitable in peptide chemistry, or d) for the preparation of a compound of the general formula Ij Ij

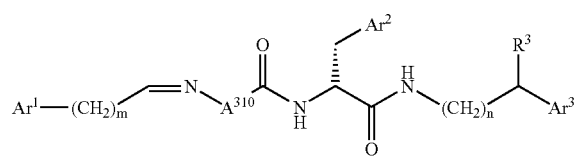

wherein $A^{310}$, $R^3$, $Ar^1$, $Ar^2$, $Ar^3$, m and n have the above meanings,
a compound,
a compound of Formula III is reacted with a compound of the general formula VIII
wherein $Ar^{110}$ and m have the above meanings, and any protective groups are each subsequently cleaved off again, and a resulting compound of Formula I if desired is converted into its acid addition salt or an acid addition salt is converted into a free compound of Formula I.

$Ar^{110}-(CH_2)_m-CHO$   VIII

According to process variant a), a compound of Formula Ig can be prepared by reacting a carboxylic acid derivative of Formula II with a primary amine of Formula III and subsequently cleaving off possibly present protective groups again. The reaction can be carried out in the manner known in peptide chemistry as a reaction in the liquid phase or alternatively as a solid-phase reaction, for example in the manner of a "Merrifield" solid-phase peptide synthesis. Where synthesis is performed in the solid phase, preferably a resin-bound compound of Formula III is reacted in a polar aprotic solvent such as N-methylpyrrolidinone (=NMP) with a compound of Formula III and also with compounds suitable as coupling reagents, in particular N-hydroxybenzotriazole (=HOBT), 2-(1H-benzotriazol-1-yl)-1,1,3,3-tetramethyluronium tetrafluoroborate (=TBTU), N-hydroxy-9-azabenzotriazole (=HOAt) and/or 2-(1H-9-azabenzotriazol-1-yl)-1,1,3,3-tetramethyluronium hexafluorophosphate (=HATU) and also in the presence of a non-nucleophilic organic base, in particular diisopropylethylamine (=DIPEA). A suitable resin for the solid-phase synthesis is in particular 2-(4-formyl-3-methoxyphenoxy)ethyl resin (=FMPE resin, cf. e.g. A. Floersheimer et al., Pept. 1990, Proc. Eur. Pept. Symp., 21st (1991), Meeting Date 1990, E. Giralt et al. (eds.) ESCOM: Leiden, 1991; 131). The resin can be loaded with the compound intended for the further reaction each time in known manner (see below).

Compounds of Formula II are known per se or may be prepared in known manner from known compounds (cf. e.g. R. Gretler et al. (1978) Helv. Chim. Acta 61(5):1730-1755). Thus for example compounds of Formula II wherein $Ar^{110}$ represents optionally protected 2-indolyl may be obtained in known manner by reductive reaction of nitrophenyl acetoacetate derivatives with titanium trichloride (cf. e.g. C. J. Moody et al. (1990) J. Chem. Soc. Perkin Trans. 1:673-679; A. Mai et al. (1999) J. Med. Chem. 42:619-627). Protective groups which are used in the context of the present invention may each be introduced in known manner and usually selectively and independently of each other and cleaved off again. Suitable protective groups for peptide synthesis are known, for example, from J. A. W. McOmie, "Protective Groups in Organic Chemistry", Plenum Press 1971, or T. W. Green and P. G. M. Wuts, "Protective Groups in Organic Synthesis", Wiley and Sons 1999. Where substituents $R^{111}$ are protected by suitable protective groups, in particular protective groups known from peptide chemistry are suitable. Preferably the tert. butylcarbonyloxy (=Boc) or the (9H-fluoren-9-ylmethoxy)carbonyl (=Fmoc) protective group is suitable.

Compounds of Formula III can for example be prepared by reacting a compound of Formula V with a compound of the general formula X

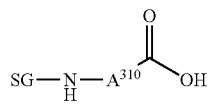

wherein $A^{310}$ has the above meaning and SG has the above meaning and is preferably the Fmoc protective group, and subsequently cleaving off the protective group SG again in known manner. The reaction may be carried out in the manner set forth above for the reaction of a compound of Formula II with a compound of Formula III, with the compound of Formula V preferably being resin-bound. Where reactive nitrogen atoms present in the group $A^{310}$ are protected by suitable protective groups, in particular the triphenylmethyl (=trityl, Trt) protective group is suitable for this. Compounds of Formula X are known per se or can be prepared in known manner from known compounds.

Compounds of Formula V can be prepared in that a compound of the general formula XI

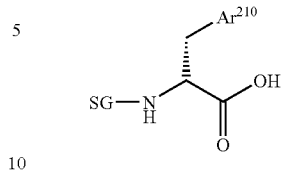

wherein $Ar^{210}$ and SG have the above meanings, is reacted with a compound of the general formula XII

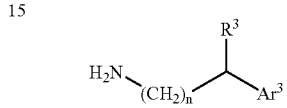

wherein $R^3$, $Ar^3$ and n have the above meanings, and a protective group SG is subsequently cleaved off again. The reaction may for example be carried out in the manner set forth above for the reaction of a compound of Formula II with a compound of Formula III, as solid-phase synthesis, with the compound of Formula XII preferably being resin-bound. Where FMPE resin is used, the resin may be loaded with a compound of Formula XII in known manner in the manner of a reductive amination (cf. B. Dörmer et al., Pept. 1998, Proc. Eur. Pept. Symp, 25$^{th}$ (1999), Meeting Date 1998; S. Bajusz et al. (eds.), Akadémiai Kiadó: Budapest, 1999; 90). Compounds of Formula XI are known per se or can be prepared in known manner from known compounds. Where substituents $Ar^{210}$ in compounds of Formula XI are protected by protective groups, in particular protective groups known from peptide chemistry are suitable. Preferably the Boc protective group is suitable. Compounds of Formula XII are known per se or can be prepared in known manner from known compounds.

In one embodiment of process variant a), a compound of the formula Ik

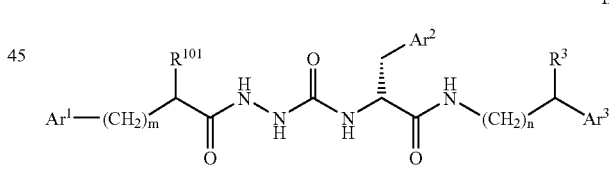

wherein $R^{101}$, $R^3$, $Ar^1$, $Ar^2$, $Ar^3$, m and n have the above meanings, can be prepared in that a carboxylic acid derivative of Formula II is reacted with a hydrazine derivative of Formula IIIa

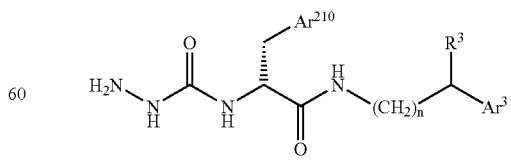

wherein $R^3$, $Ar^{210}$, $Ar^3$ and n have the above meanings, and possibly present protective groups are subsequently cleaved off again. The reaction may for example be carried out in the manner set forth above for the reaction of a compound of Formula II with a compound of Formula III, as solid-phase synthesis. Compounds of Formula IIIa can be prepared by reacting a compound of Formula V with known 5-(9H-fluoren-9-ylmethoxy)-3H-[1,3,4]oxadiazol-2-one and subsequently cleaving off undesirable protective groups. The reaction may for example be carried out in the manner set forth above for the reaction of a compound of Formula II with a compound of Formula III, as solid-phase synthesis, with dichloromethane in particular possibly being used as solvent.

According to process variant b), a compound of Formula Ih can be prepared by reacting a carboxylic acid derivative of Formula IV with a primary amine of Formula V and subsequently cleaving off possibly present protective groups again. The reaction may for example be carried out in the manner set forth above for the reaction of a compound of Formula II with a compound of Formula III, as solid-phase synthesis or alternatively in liquid phase. Where the reaction is carried out in solid phase, preferably the compound of Formula V is resin-bound. Where the reaction is carried out in liquid phase, it is possible to work in a polar aprotic solvent such as dimethyl formamide (=DMF) and in the presence of compounds suitable as coupling reagents given under process variant a), and in the presence of a non-nucleophilic organic base, in particular sym. collidine. Where $R^{201}$ represents an amino protective group, this may preferably be the Fmoc protective group. Where substituents $R^{10}$ are protected by suitable protective groups, the protective groups given above as being suitable for substituents $R^{111}$ are suitable. Compounds of Formula IV can be prepared by reacting a compound of the general formula XIII

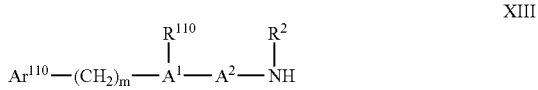

XIII wherein $A^1$, $A^2$, $R^{110}$, $R^2$, $Ar^{110}$ and m have the above meanings, with a compound of the general formula XIV

XIV wherein $A^{311}$ has the above meaning, X stands for a cleavable leaving group and $SG^1$ stands for a carboxylic acid protective group, subsequently cleaving off a carboxylic acid protective group $SG^1$ again in known manner and if necessary introducing a protective group into substituents $R^2$. The reaction may be carried out in an aromatic solvent such as toluene at temperatures between −20° C. and room temperature (=RT), preferably at 0° C. In particular halogen, preferably chlorine or bromine, is used as leaving group X in compounds of Formula XIV. A suitable carboxyl protective group $SG^1$ is in particular lower alkyl, preferably ethyl or tert. butyl. Compounds of Formula XIII are known per se or can be prepared in known manner from known compounds. Compounds of Formula XIV are known per se or can be prepared in known manner from known compounds.

According to process variant c), a compound of Formula Ii can be prepared by reacting a primary amine of Formula V with a carbonyl-group synthesis equivalent and with a hydrazine derivative of Formula VI and subsequently cleaving off possibly present protective groups again. The reaction may preferably be carried out at room temperature in the liquid phase, in particular in a dipolar aprotic solvent such as dichloromethane. Expediently, operation is in the presence of an organic non-nucleophilic base which is soluble in the solvent, such as 4-dimethylaminopyridine (=DMAP). Suitable carbonyl-group synthesis equivalents are preferably dipentafluorophenyl carbonate or alternatively phosgene, bis-(trichloromethyl)carbonate (=triphosgene), trichloromethyl chloroformate (=diphosgene) or carbonyl diimidazole. Compounds of Formula VI are known per se, or can be prepared in known manner from known compounds. Thus for example a compound of the general formula VIa

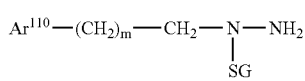

VIa wherein $Ar^{110}$, m and SG have the above meanings, can be prepared in known manner by reductive amination from a corresponding aldehyde of the general formula VIII and a corresponding amine of the general formula XVII

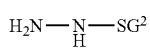

XVII wherein $SG^2$ represents a protective group known in peptide chemistry, preferably the Boc protective group, subsequent introduction of a protective group SG and finally cleavage of the protective group $SG^2$. The reaction may be carried out in a dipolar aprotic solvent such as tetrahydrofuran (=THF) and preferably at room temperature. The reduction of a corresponding imine compound obtained as intermediate product can be carried out in a dipolar-aprotic solvent such as THF and at temperatures between −20° C. and room temperature, preferably at 0° C. Suitable reducing agents are complex borohydrides such as $NaCNBH_3$. The compounds of Formulae VIII and XVII are known per se or can be prepared from known compounds in known manner.

According to process variant d), a compound of Formula Ij can be prepared by reacting an amino compound of Formula III with an aldehyde of Formula VIII and subsequently cleaving off possibly present protective groups again. The reaction can be carried out in the manner set forth above for the reaction of compounds of Formula XVI with compounds of Formula XVII, the resulting imine in this case however not being reduced.

The resulting compounds of Formula I may in each case be isolated from the reaction mixture and purified in known manner. Acid addition salts may be converted into the free bases in conventional manner, and these may if desired be converted in known manner into physiologically compatible acid addition salts.

Physiologically compatible salts of compounds of Formula I are their salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid.

The compounds of Formula I may in addition to the carbon atom bearing the —$CH_2$—$Ar^2$ radical also contain further chiral centres, namely the carbon atom bearing the substituent $R^3$, the carbon atom, substituted by $C_{1-4}$ alkyl or by $C_{1-4}$ alkyl carbonylamide, of the methylene group $A^3$ and/or the carbon atom of the CH group $A^1$, where $R^1$ is amino. The compounds of Formula I may thus be present in several stereoisomeric forms. The present invention comprises both the mixtures of optical isomers and the isomerically pure compounds of Formula I. Isomerically pure compounds of Formula I are preferred, in particular the compounds of Formula I, wherein the carbon atom, substituted by $C_{1-4}$-alkyl or by $C_{1-4}$ alkyl carbonylamide, of the methylene group $A^3$ is in the S configuration. Where mixtures of optical isomers of the starting compound are used in the synthesis of the compounds of Formula I, the compounds of Formula I are also obtained in the form of mixtures of optical isomers. Departing from stereochemically uniform forms of the starting compound, stereochemically uniform compounds of Formula I can also be obtained. The stereochemically uniform compounds of Formula I can also be obtained from the mixtures of optical isomers in known manner, for example by chromatographic separation on chiral separating materials or by reaction with suitable optically active acids, for example tartaric acid or 10-camphorsulfonic acid, and subsequent separation into their optically active antipodes by fractional crystallisation of the diastereomeric salts obtained.

The novel compounds of Formula I and their physiologically compatible acid addition salts are distinguished by a high affinity to the bombesin receptor of subtype 3 which is selective in comparison to other known bombesin receptor subtypes, NMB-R and GRP-R, on which they act as agonists. It can therefore be expected that the compounds of Formula I are suitable for the treatment and/or inhibition of clinical conditions which can be beneficially influenced by stimulation of the BRS-3. In particular, the compounds according to the invention appear to be suitable for treatment and/or inhibition of obesity (=adiposity), diabetes, hyperinsulinism, cardiovascular diseases, eating disorders (hyperphagia, anorexia, bulimia) and/or syndrome X.

Description of the Pharmacological Test Method:

The BRS-3-agonistic effects of the test substances can for example be demonstrated in vitro in a pharmacological standard test operating in accordance with the FLIPR method ("Fluorometric Imaging Plate Reader"). For this, CHO cells (="Chinese hamster ovary cells") initially were transfected in known manner with an expression vector for the subtype 3 of the human bombesin receptor, i.e. BRS-3.

The cDNA of the human BRS-3 (nucleotide sequence under GenBank Accession No. L08893) was excised from the plasmid vector pGEM4 (from Promega, USA) using the restriction endonuclease EcoRI and was subcloned into the expression vector pcDNA3.1(−) (from Invitrogen, USA). CHO-K1 cells, which were already stably transfected with the expression vector RD-HGA16, which bears the cDNA sequence of the human Gα16 protein (nucleotide sequence under GenBank Accession No. M63904), were placed in sample plates with 24 sample wells ("24-well plate") and incubated overnight under sterile conditions in an air-humidified incubator at 37° C. and 5% $CO_2$ in F-12 medium plus Glutamax-I (from GibcoBRL, cat. No. 31765), to which 10%-strength foetal calf serum (inactivated at 56° C. for 1 h, from GibcoBRL), 25 µg/ml gentamicin (from GibcoBRL) and 0.2 mg/ml hygromycin B (from GibcoBRL) had been added. The next day, the cells were transfected with the BRS-3 expression vector by adding, using the "Effectene Transfection Reagent" (from Qiagen), 12 µl of a solution containing 0.3 µg/µl DNA of the expression vector per sample well. One day after transfection, the culture medium was replaced by selection medium. For this, the transfected cells, which each simultaneously express BRS-3 and the human Gα16 protein, were cultivated under sterile conditions at 37° C. and 5% $CO_2$ in F-12 medium plus Glutamax-I (from GibcoBRL, cat. No. 31765), to which 10%-strength foetal calf serum (inactivated at 56° C. for 1 h, from GibcoBRL), 25 µg/ml gentamicin (from GibcoBRL), 0.2 mg/ml hygromycin B (from GibcoBRL) and 0.5 mg/ml geneticin (from GibcoBRL) had been added. To optimize the cell test, the cells with the highest receptor expression rate were selected. For this, the transfected cells were diluted 1:30,000 with the selection medium described above and were placed in sample plates with 96 sample wells ("96-well plate"). The cells were incubated overnight at 37° C. and 5% $CO_2$, then those sample wells which contained only an individual cell were selected. These cells were first started in sample plates with 24 sample wells ("24-well plate") and then cultivated in Costar plastic flasks (first 25 ml and then 225 ml). The BRS-3 receptor expression of the respective individual cell clone was estimated by determination of the $EC_{50}$ value of the synthetic nonapeptide [D-Phe$^6$,β-Ala$^{11}$, Phe$^{13}$,Nle$^{14}$]Bn(6-14) as ligand (for performance of the test see below). The transfected cells were stored at −80° C. in aliquots of 1.8 ml medium each with 10% dimethyl sulfoxide (=DMSO) (cell concentration 1×10$^6$ cells/ml). For cultivation, a frozen aliquot was heated to 37° C., transferred into a Costar plastic flask (225 ml) and diluted with 50 ml of the selection medium described above. The medium was first changed once after 30 minutes' incubation. On each following first to third day, the medium was removed, the adherent cells (40-95% confluence) were washed with PBS Dulbecco's (from GibcoBRL) and detached from the bottom of the flask by a 2-minute treatment with trypsin-EDTA solution (from GibcoBRL) at 37° C. If the cells were to be cultivated further, they were transferred into a new plastic flask with fresh medium. If experiments were to be carried out with the cells, the cells were transferred into Costar sample plates with 96 sample wells, a clear baseplate and cover ("Costar 96-well assay plates", from Corning), once the cell concentration had been set to 1.2×10$^4$ cells/ml.

BRS-3 is coupled via G-proteins to the $Ca^{2+}$-signal transduction path of the CHO cell. If an agonist binds to the receptor, the phospholipase C is activated via the G-protein, and then in turn catalyses the synthesis of water-soluble inositol phosphates. These water-soluble inositol phosphates cause $Ca^{2+}$ to be released, which is stored in the endoplasmic reticulum. The transient increase in the cytosolic $Ca^{2+}$ concentration was measured in what is called the FLIPR experiment. To this end, the cells were laden with a $Ca^{2+}$-binding, fluorescent dye, Fluo4 (from Molecular Probes). This intracellular dye binds the cytosolic $Ca^{2+}$ ions released after activation and in so doing intensifies its fluorescent intensity. The change in fluorescent intensity is proportional to the change in the intracellular $Ca^{2+}$ concentration and is a measurement of the activation of the cell by the corresponding agonists. Below the maximum fluorescence response, the degree of activation is dependent on the concentration of the compounds used. The change in fluorescence due to activation of BRS-3 was determined for each substance to be tested at different substance concentrations. The maximum fluorescence response upon activation of the BRS-3 with the synthetic nonapeptide [D-Phe$^6$, α-Ala$^{11}$,Phe$^{13}$,Nle$^{14}$]Bn(6-14) served as reference value for 100% activation [cf. Mantey et al. (1997) *J. Biol. Chem.* 272:26062-26071]. The concentration of the compound at which 50% activation occurred was determined as $EC_{50}$ value and served as a measure of the effectiveness of the respective test compound as BRS-3 agonist.

The transfected CHO cells were cultivated for 18 to 24 hours (=h) in the "Costar 96-well assay plates" (from Corning) until they were confluent. A 250 mM stock solution of probenecid was freshly prepared each day. For this, 710 mg probenecid (from Sigma # P8761) was dissolved in 5 ml 1 N NaOH and then diluted to 10 ml with HBSS medium without phenol red (GibcoBRL), which contained 20 mM HEPES (from PAA Laboratories). A 2 mM stock solution of the fluorescent calcium-ion indicator dye Fluo4 was prepared by dissolving 1 mg Fluo4 in 440 µl DMSO and was stored at −20° C. Furthermore, a 20%-strength (w/v) solution of Pluronic F-127 (from Sigma) in DMSO was used. Immediately before use, a 22 µl aliquot of the Fluo4 stock solution was thawed. The loading medium was always freshly prepared by mixing 42 ml HBSS medium without phenol red (GibcoBRL), which contained 60 mM HEPES (from PAA Laboratories), with 420 µl of the probenecid stock solution and 22 µl of each of Fluo4 stock solution and Pluronic F-127 solution. The cells were each incubated per sample well with 100 µl fresh loading medium for 45-60 min at 37° C. and 5% $CO_2$. Then the cells were washed three times with 100 µl HBSS medium with 20 mM HEPES and 2.5 mM probenecid each time. Following the final washing step, 100 µl volume remained on the cells in each of the 96 sample wells.

In each case 10 mM stock solutions in DMSO were prepared of the compounds of Formula I, of which dilution series with HBSS medium with 20 mM HEPES were loaded into microtitration plates with 96 sample wells ("96-well plates", from Greiner). The maximum concentration used in the measurements was usually 33 µM, but in some cases also only 1 µM. The solutions were diluted 1:2, 1:3, 1:4 or 1:10 on 8 or 16 different sample wells, according to the respective compound. Each microtitration plate contained as a reference a dilution series of the nonapeptide [D-Phe$^6$,β-Ala$^{11}$, Phe$^{13}$, Nle$^{14}$]Bn(6-14).

The FLIPR apparatus (from Molecular Devices) was programmed to measure the background fluorescence over a period of 30 seconds (=sec.) at 6-second intervals. After transferring 50 µl in each case from each sample well of the microtitration plate into the corresponding sample well of the cell plate, the change in fluorescence over a period of 100 seconds (=sec.) was plotted at 1-second intervals, and at 6-second intervals during the final 42 sec.

The changes in fluorescence of the reference compound as a function of the concentration were plotted, and the peptide concentration of the nonapeptide at which the maximum change in fluorescence had already been observed was determined (usually 16 µM). The value of the maximum change in fluorescence per sample well was exported to the Excel spreadsheet program (from Microsoft) and standardised using the maximum value of the change in fluorescence for the corresponding reference compound, which was adopted as 100% value. The curves for the gradient of the relative change in fluorescence dependent on the concentration of the compound to be investigated and the corresponding $EC_{50}$ value were calculated using the Graphpad Prism program (Version 3.00, from Graphpad Software).

In the pharmacological FLIPR test described above, all the example compounds given below exhibited $EC_{50}$ values (in nM) which were less than or equal to 2600. The compounds of Examples 13 to 34 exhibited $EC_{50}$ values which were less than or equal to 710. The $EC_{50}$ values determined in the FLIPR experiment described above are listed in the following Table 1 for individual compounds of Formula I. The example numbers given in Table 1 relate to the following preparative examples.

TABLE 1

| Agonistic activity of the test substances on BRS-3 | |
|---|---|
| Example No. | $EC_{50}$ [nM] |
| 2 | 2.1 |
| 3 | 4.0 |
| 4 | 1.4 |
| 5 | 6.0 |
| 6 | 1.5 |
| 7 | 30 |
| 15 | 57 |
| 19 | 32 |
| 21 | 21 |
| 22 | 2.9 |
| 23 | 21 |
| 24 | 17 |
| 26 | 25 |
| 27 | 3.1 |
| 28 | 0.19 |
| 30 | 2.2 |

The compounds of Formula I may be administered in conventional pharmaceutical preparations. The doses to be used may vary individually and will naturally vary according to the type of condition to be treated and the substance used. In general, however, medicinal forms with an active substance content of 0.1 to 300 mg per individual dose are suitable for administration to humans and larger mammals.

The compounds to Formula I may be contained according to the invention, together with conventional pharmaceutical auxiliaries and/or exipients, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic excipients, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or excipients in known manner. For the preparation of solid medicament forms, the active substances may for example be mixed with the auxiliaries and/or excipients in conventional manner and may be wet or dry granulated. The granules or powder may be poured directly into capsules or be pressed into tablet cores in conventional manner. These may be coated in known manner if desired.

The following examples are intended to explain the invention further, without limiting its scope.

EXAMPLE 1

N1-[(1R)-2-(1H-3-indolyl)-1-(phenethylcarbamoyl)-ethyl]-(2S)-2-{[(1R)-1-amino-2-phenethyl]-carboxamido}-pentane diamide; (H-D-Phe-Gln-D-Trp-phenylethylamide)

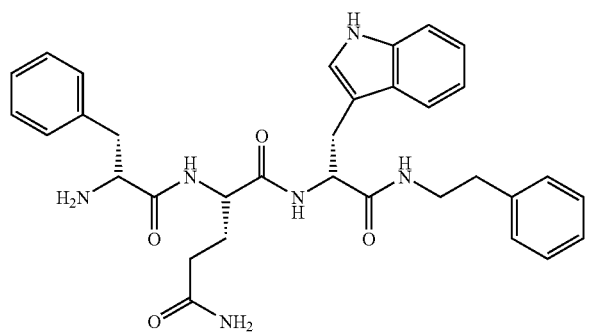

100 mg FMPE resin (maximum capacity 0.54 mmol/g) was allowed to swell in 1 ml dichloroethane for 10 min. 0.5 ml trimethyl orthoformate (=TMOF), 68 µl 2-phenylethylamine and 114 mg NaBH(OAc)$_3$ were added to this receiving solution, the resulting mixture was treated for 10 min. with ultrasound and then shaken overnight at RT. Then the resin was washed in succession three times for three min. with 3 ml dichloromethane each time and three times for three min. with 3 ml NMP each time. Then a solution of 56 mg Fmoc-D-Trp(Boc)-OH, 41 mg HATU, 14.6 mg HOAt and 143 µl sym. collidine in 1 ml NMP was added to the washed resin. The resin was shaken in this solution for 5 h at RT, washed three times for three min. with 3 ml NMP each time and the resin was again treated overnight with a solution of 56 mg Fmoc-D-Trp(Boc)-OH, 41 mg HATU, 14.6 mg HOAt and 143 µl sym. collidine in 1 ml NMP. Finally the resin was washed three times for three min. with 1 ml dichloromethane each time and was dried in an oil pump vacuum. 129 mg of an FMPE resin laden with Fmoc-D-Trp(Boc)-phenylethylamide [loading 0.366 mmol/g; corresponding to 30 mg (0.047 mmol) free Fmoc-D-Trp(Boc)-phenylethylamide], which was used directly without cleavage of the intermediate product for the reaction below.

A) The entire amount of the laden FMPE resin obtained above [laden with 0.366 mmol/g Fmoc-D-Trp(Boc)-phenylethylamide, corresponding to 30 mg (0.047 mmol) of the free compound] was allowed to swell for 10 min. in 5 ml NMP. Then the FMPE resin was treated for 15 min. with 5 ml of a freshly prepared 20%-strength (v/v) solution of piperidine in NMP, was washed five times for three min. with 5 ml NMP each time and the FMPE resin was finally treated again for 15 min. with 5 ml of a freshly prepared 20%-strength (v/v) solution of piperidine in NMP. Finally, the resin was washed five times for three min. with 5 ml NMP each time. The resulting FMPE resin laden with D-Trp(Boc)-phenylethylamide was used directly for the reaction below without isolating the intermediate product.

B) The entire amount of the laden FMPE resin obtained above [at assumed 100% conversion laden with 0.366 mmol/g D-Trp(Boc)-phenylethylamide, corresponding to 19.2 mg (0.047 mmol) of the free compound] was washed five times for three min. with 5 ml NMP each time. Then a solution of 57.4 mg Fmoc-Gln(Trt)-OH, 12.7 mg HOBT×H$_2$O and 30 mg TBTU in 2 ml NMP was added to the laden FMPE resin. Finally 46 µl DIPEA was added to the resulting receiving solution and the mixture was shaken for 45 min. Once the FMPE resin had been washed five times for three min. with 5 ml NMP each time, the coupling step described above was repeated. Finally it was washed another five times for three min. with 5 ml NMP each time. An FMPE resin laden with Fmoc-Gln(Trt)-D-Trp(Boc)-phenylethylamide was obtained, which was used directly for the reaction below without isolating the intermediate product.

D) The entire amount of the laden FMPE resin obtained above [at assumed 100% conversion laden with 0.366 mmol/g Fmoc-Gln(Trt)-D-Trp(Boc)-phenylethylamide, corresponding to 47 mg (0.047 mmol) of the free compound] was treated to cleave off the Fmoc protective group as described above under B). An FMPE resin laden with Gln(Trt)-D-Trp(Boc)-phenylethylamide was obtained, which was used directly for the reaction below without isolating the intermediate product.

E) The entire amount of the laden FMPE resin obtained above [at assumed 100% conversion laden with 0.366 mmol/g Gln(Trt)-D-Trp(Boc)-phenylethylamide, corresponding to 36.6 mg (0.047 mmol) of the free compound] was washed five times for three min. with 5 ml NMP each time. Then a solution of 36.4 mg Fmoc-Phe-OH, 12.7 mg HOBT×H$_2$O and 30 mg TBTU in 2 ml NMP was added to the laden FMPE resin. Finally 46 µl DIPEA was added to the resulting receiving solution and the mixture was shaken for 45 min. Once the FMPE resin had been washed five times for three min. with 5 ml NMP each time, the coupling step described above was repeated. Finally it was washed another five times for three min. with 5 ml NMP each time. An FMPE resin laden with Fmoc-Phe-Gln(Trt)-D-Trp(Boc)-phenylethylamide was obtained, which was used directly for the reaction below without isolating the intermediate product.

F) The entire amount of the laden FMPE resin obtained above [at assumed 100% conversion laden with 0.366 mmol/g Fmoc-Phe-Gln(Trt)-D-Trp(Boc)-phenylethylamide, corresponding to 54 mg (0.047 mmol) of the free compound] was treated to cleave off the Fmoc protective group as described above under B). An FMPE resin laden with Phe-Gln(Trt)-D-Trp(Boc)-phenylethylamide was obtained, which was used directly for the reaction below without isolating the intermediate product.

G) The entire amount of the laden FMPE resin obtained above [at assumed 100% conversion laden with 0.366 mmol/g Phe-Gln(Trt)-D-Trp(Boc)-phenylethylamide, corresponding to 43.5 mg (0.047 mmol) of the free compound] was washed three times for ten min. with 3 ml dichloromethane each time. Then the laden FMPE resin was treated three times for 30 min. with 2 ml each time of a mixture of trifluoroacetic acid (=TFA)/triisopropylsilane (=TIPS)/H$_2$O (18:1:1 v/v/v) and the FMPE resin was filtered off. Then it was again washed three times for three min. with 3 ml dichloromethane each time and the FMPE resin was filtered off. The combined filtrates were evaporated in a water pump vacuum with nitrogen-cooled receiving solution. The remaining residue was taken up in DMSO and purified by reversed-phase HPLC [HPLC system from *Amersham Pharmacia Biotech* Äkta Basic 100F; pump system P-900 and detector UV-900; column ODS-A C$_{18}$ from *Omnicrom YMC* (250 mm×20 mm, 10 µm, flow rate: 8 ml/min); elution with linear gradient (30 min.) of water (solvent A) in acetonitrile (solvent B) and 0.1% (v/v) TFA]. Freeze-drying of the purified fractions yielded 19.2 mg of the title compound as colorless powder.

HPLC-MS (ESI) m/z 276.1 (32), 308.1 (90), 583.3 (72) [m+H]$^+$, 605.4 (100) [m+Na]$^+$, 893.6 (13), 1165.2 (10) [2 m+H]$^+$, 1187.2 (40) [2m+Na]$^+$.

EXAMPLE 2

N1-phenethyl-(2R)-2-[(1S)-1-(benzylcarboxamido)-ethyl]-carboxamido-3-(1H-3-indolyl)-propanamide

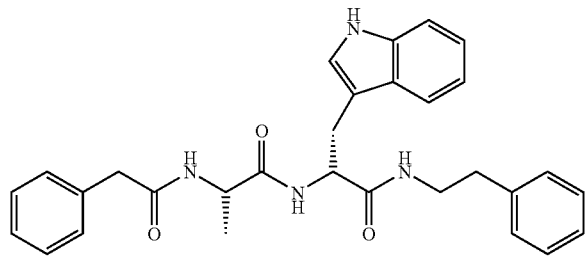

A) 100 mg of an FMPE resin laden with Fmoc-D-Trp(Boc)-phenylethylamide [for preparation see Example 1A); loading 0.354 mmol/g; corresponding to 22.3 mg (0.035 mmol) free Fmoc-D-Trp(Boc)-phenylethylamide] was reacted in a manner corresponding to Example 1B. The resulting resin-bound Trp(Boc)-phenylethylamide was used directly for the reaction below without isolation or purification.

B) The entire amount of the FMPE resin laden with D-Trp(Boc)-phenylethylamide obtained above [at assumed 100% conversion laden with 0.354 mmol/g D-Trp(Boc)-phenylethylamide, corresponding to 14.4 mg (0.035 mmol) of the free compound] was washed five times for three min. with 5 ml NMP each time. Then a solution of 22 mg Fmoc-Ala-OH, 9.5 mg HOBT×H$_2$O and 22.5 mg TBTU in 2 ml NMP was added to the laden FMPE resin. Finally 34 μl DIPEA was added and the resulting mixture was shaken for 45 min. Once the FMPE resin had been washed five times for three min. with 5 ml NMP each time, the coupling step described above was repeated. Finally it was washed another five times for three minutes with 5 ml portions of NMP. An FMPE resin laden with Fmoc-Ala-D-Trp(Boc)-phenylethylamide was obtained, which was used directly for the reaction below without isolation.

C) The entire amount of the laden FMPE resin obtained above [at assumed 100% conversion laden with 0.354 mmol/g Fmoc-Ala-D-Trp(Boc)-N-phenylethylamide, corresponding to 24.5 mg (0.035 mmol) of the free compound] was treated to cleave off the Fmoc protective group as described above under Example 1B). An FMPE resin laden with Ala-D-Trp(Boc)-phenylethylamide was obtained, which was used directly for the reaction below without isolation.

D) The entire amount of the laden FMPE resin obtained above [at assumed 100% conversion laden with 0.354 mmol/g Ala-D-Trp(Boc)-phenylethylamide, corresponding to 16.7 mg (0.035 mmol) of the free compound] was washed five times for three min. with 5 ml NMP each time. Then a solution of 9.6 mg phenylacetic acid, 9.5 mg HOBT×H$_2$O and 22.5 mg TBTU in 2 ml NMP was added to the laden FMPE resin. Finally 34 μl DIPEA was added and the resulting mixture was shaken for 45 min. Once the FMPE resin had been washed five times for three min. with 5 ml NMP each time, the coupling step described above was repeated. Finally it was washed another five times for three min. with 5 ml NMP each time. An FMPE resin laden with phenyl acetate-Ala-D-Trp(Boc)-phenylethylamide was obtained, which was used directly for the reaction below without isolation.

E) The entire amount of the laden FMPE resin obtained above [at assumed 100% conversion laden with 0.354 mmol/g phenyl acetate-Ala-D-Trp(Boc)-N-phenylethylamide, corresponding to 20.9 mg (0.035 mmol) of the free compound] was treated to cleave off the FMPE resin and remove the Boc protective group as described above in Example 1G). Purification of the resulting crude product by HPLC and subsequent freeze-drying yielded 12.6 mg (0.025 mmol) of the title compound as colorless powder with a melting point of 205-207° C.

$^1$H-NMR (500 MHz, DMSO-d$_6$, 300 K) δ=10.78 (s, 1H, NH—CH—C), 8.24 (d, J$_{HH}$=6.8 Hz, 1H, NH—CH—CH$_3$), 8.18 (d, J=8.4 Hz, 1H, NH—CH—CH$_2$), 8.00 (t, J=5.5 Hz, 1H, NH—CH$_2$—CH$_2$), 7.57 (d, J=7.9 Hz, 1H, arom), 6.95-7.32 (m, 14H, arom), 4.38-4.43 (m, 1H, NH—CH—CH$_2$), 4.21-4.25 (m, 1H, NH—CH—CH$_3$), 3.45 (s, 2H, CO—CH$_2$), 3.19-3.24 (m, 2H, NH—CH$_2$—CH$_2$), 3.11 (dd, J=14.7 Hz, J=4.6 Hz, 1H, NH—CH—CH$_2$), 2.84 (dd, J=14.6 Hz, J=9.6 Hz, 1H, NH—CH—CH$_2$), 2.61 (t, J=7.6 Hz, 2H, NH—CH$_2$—CH$_2$), 1.01 (d, J=7.0 Hz, 3H, CH$_3$). HPLC-MS (ESI) m/z 159.1 (40), 291.2 (35), 308.1 (100), 497.2 (80) [M+H]$^+$, 519.4 (55) [M+Na]$^+$, 764.5 (20), 993.1 (10) [2M+H]$^+$, 1015.2 (100) [2M+Na]$^+$.

EXAMPLE 3

N1-phenethyl-(2R)-2-{1-[(4-chlorobenzyl)-amino]-ethylcarboxamido}-3-(1H-3-indolyl)-propanamide

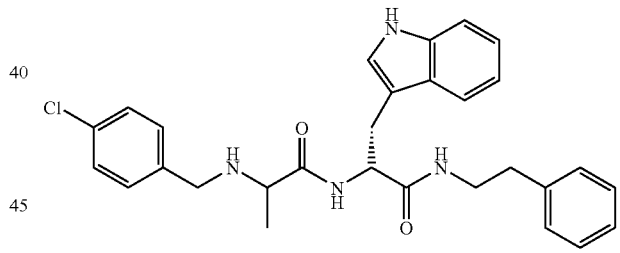

A) A solution of 8.35 g ethyl 2-bromopropionate in 18 ml toluene was added dropwise to a solution of 7.08 g 4-chlorobenzylamine and 5.06 g triethylamine in 38 ml toluene with stirring and ice cooling over a period of 4 h, and the reaction mixture was then stirred for 4 days. Then the organic phase was extracted with 300 ml water and then dried over Na$_2$SO$_4$. The solvent was evaporated in a water pump vacuum and the resulting residue was purified by flash chromatography at a pressure of 1-1.2 bar (stationary phase: Silicagel 60, grain size 0.040-0.063 mm, mobile phase: ethyl acetate/hexane 1:1). After concentration of the solvent in a water pump vacuum and drying of the residue in an oil pump vacuum, 4.25 g N-(4-chlorobenzyl)-alanine ethyl ester was obtained as yellow oil.

$^1$H-NMR (250 MHz, DMSO-d$_6$, 300 K) δ=7.31-7.38 (m, 4H, arom), 4.09 (q, J=7.1 Hz, 2H, CH$_2$—CH$_3$), 3.65 (q, J=13.9 Hz, NH—CH$_2$—C$_6$H$_4$Cl), 3.20-3.24 (m, 1H, NH—CH), 2.51 (bs, 1H, NH), 1.17-1.22 (m, 6H, CH$_2$—CH$_3$ and CH—CH$_3$).

B) 6.2 ml 1 N NaOH and 12 ml methanol were added to 1.0 g of the N-(4-chlorobenzyl)-alanine ethyl ester obtained above and the mixture was stirred for 30 min. It was neutralised with 1 N HCl and the solvent was evaporated in a water pump vacuum. The resulting residue was taken up in a mixture of 15 ml saturated aqueous NaHCO₃ solution and 4 ml dioxane. A solution of 1.1 g FmocCl in 8 ml dioxane was added dropwise to this receiving solution over a period of 15 min. with ice cooling. The reaction mixture was stirred for 30 min. with ice cooling and then overnight at RT. Then 20 ml water was added to the reaction mixture, the aqueous phase was separated and extracted with 100 ml diethyl ether. The aqueous phase was set to pH 1 by addition of concentrated hydrochloric acid and then extracted again three times with 100 ml ethyl acetate each time. The combined organic phases were dried over Na₂SO₄ and the solvent was evaporated in a water pump vacuum. The resulting residue was purified by column chromatography (stationary phase: Silicagel 60, grain size 0.040-0.063 mm, mobile phase: ethyl acetate/hexane/acetic acid 1:1:1). After evaporating the solvent in a water pump vacuum and drying the residue in an oil pump vacuum, 1.3 g 2-{4-chlorobenzyl-[(9H-fluoren-9-ylmethoxy)-carbonyl]-amino}-propanoic acid was obtained as colorless oil (2.98 mmol). The ratio of cis/trans-isomers was not determined.

HPLC-MS (ESI) m/z 179.1 (95), 436.0 (75) [M+H]⁺, 458.2 (40) [M+Na]⁺, 893. .0 (50) [2M+Na]⁺, 909.2 (100) [2M+K]⁺.

C) 0.26 g phenylethylamine, 1.13 g Fmoc-D-Trp(Boc)-OH, 0.43 g HOBT and 1.03 g TBTU were dissolved in 15 ml DMF. 1.19 g DIPEA was added dropwise to this receiving solution over a period of 5 min. Then the reaction mixture was stirred for one hour, the solvent was evaporated in a water pump vacuum and the resulting residue was purified by flash chromatography at a pressure of 1-1.2 bar (stationary phase: Silicagel 60, grain size 0.040-0.063 mm, mobile phase: ethyl acetate/hexane 1:1). After evaporating the solvent in a water pump vacuum and drying the residue in an oil pump vacuum, 1.33 g N-1-phenethyl-(2R)-2-(9H-fluoren-9-ylmethoxy)-carboxamido-3-[1-(tert-butoxycarbonyl)-3-indolyl]-propanamide (=Fmoc-D-Trp(Boc)-phenylethylamide) was obtained as colorless, waxy solid with a melting point of 140° C.

HPLC-MS (ESI) m/z 308.2 (20), 530.3 (40), 630.3 (40) [M+H]⁺, 652.4 (10) [M+Na]⁺, 1259.5 (100) [2M+H]⁺, 1281.5 (30) [2M+Na]⁺.

D) 1.0 g of the Fmoc-D-Trp(Boc)-phenylethylamide obtained above was dissolved in 6 ml of a 20%-strength (v/v) solution of piperidine in DMF. The reaction mixture was stirred for 30 min. and the solvent was then evaporated off in a water pump vacuum with nitrogen-cooled receiving solution. The remaining residue was separated from the resulting Fmoc-piperidine complex by flash chromatography at a pressure of 1-1.2 bar (stationary phase: Silicagel 60, grain size 0.040-0.063 mm, mobile phase: ethyl acetate/hexane 2:1) and then eluted (mobile phase: chloroform/methanol 15:1). Concentrating the solvent in a water pump vacuum and drying the residue in an oil pump vacuum yielded 0.63 g tert-Butyl-3-[(2R)-2-amino-2-(phenethylcarbamoyl)-ethyl]-1H-1-indole carboxylate (=D-Trp(Boc)-phenylethylamide) as yellow oil.

MS (ESI) m/z 159.1 (20), 291.2 (75), 308.1 (95), 352.1 (70), 408.1 (100) [M+H]⁺, 430.1 (35) [M+Na]⁺, 815.2 (15) [2M+H]⁺, 837.1 (20) [2M+Na]⁺.

E) 0.32 g 2-{4-chlorobenzyl-[(9H-fluoren-9-ylmethoxy)-carbonyl]-amino}-propanoic acid (0.736 mmol, for preparation see above under B), 0.30 g tert-butyl-3-[(2R)-2-amino-2-(phenethylcarbamoyl)ethyl]-1H-1-indole carboxylate, for preparation see above under D), 0.42 g HATU and 0.15 g HOAt were dissolved in 7 ml DMF. Then 1.33 g sym. collidine was added dropwise over a period of 10 min. The reaction mixture was stirred for 1 h and then the solvent was evaporated in a water pump vacuum with nitrogen cooling. The remaining residue was purified by flash chromatography at a pressure of 1-1.2 bar (stationary phase: Silicagel 60, grain size 0.040-0.063 mm, mobile phase: ethyl acetate/hexane 1:1). Concentrating the solvent in a water pump vacuum and drying the residue in an oil pump vacuum yielded 0.54 g N1-phenethyl-(2R)-2-{1-[N-(4-chlorobenzyl)-N-(9H-fluoren-9-ylmethoxycarbonyl)-amino]-ethylcarboxamido}-3-[1-(tert-butoxycarbonyl)-3-indolyl]-propanamide as colorless foam.

MS (ESI) m/z 179.2 (10), 769.4 (10), 825.4 (100) [m+H]⁺, 1651.6 (55) [2m+H]⁺.

F) The entire amount (0.54 g) of the N1-phenethyl-(2R)-2-{1-[N-(4-chlorobenzyl)-N-(9H-fluoren-9-ylmethoxycarbonyl)-amino]-ethylcarboxamido}-3-[1-(tert-butoxycarbonyl)-3-indolyl]-propanamide obtained above (0.654 mmol) was dissolved in 2.5 ml dichloromethane. 0.25 ml triisopropylsilane was added to this receiving solution and the resulting mixture was cooled to 0° C. Then 2.5 ml TFA was added dropwise to the mixture over a period of 5 min. and the mixture was stirred for 1 h at 0° C. The solvent was evaporated in a water pump vacuum with nitrogen-cooled receiving solution. The remaining residue was taken up in a mixture of 20 ml DMSO, 2.5 ml water and 2.5 ml acetic acid and stirred overnight at RT. Then the solvent was evaporated in a water pump vacuum and the N1-phenethyl-(2R)-2-{1-[N-(4-chlorobenzyl)-N-(9H-fluoren-9-ylmethoxycarbonyl)-amino]-ethylcarboxamido}-3-[1H-3-indolyl]-propanamide remaining as residue was used directly for the reaction given below without further purification or characterisation.

G) The entire amount of the Fmoc-protected propanamide obtained above (0.654 mmol at 100% conversion) was dissolved in 10 ml of a 20%-strength (v/v) solution of piperidine in DMF and stirred for 30 min. The solvent was evaporated in a water pump vacuum with nitrogen-cooled receiving solution and the resulting residue was purified by flash chromatography at a pressure of 1-1.2 bar (stationary phase: Silicagel 60, grain size 0.040-0.063 mm, mobile phase: ethyl acetate). After freeze-drying the purified fractions, 320 mg of the title compound (0.637 mmol) was obtained as colorless powder with a melting point of 107-110° C. The ratio of the two isomers to one another was 1:1.24.

¹H-NMR (500 MHz, DMSO-d₆, 300 K) δ=10.85 and 10.83 (s, 1H, NH—CH—C), 9.2 (m, 1H, NH—CH—CH₃), 8.72 and 8.77 (d, J=8.5 Hz, 1H, NH—CH—CH₂), 8.28 and 8.34 (t, J=5.5 Hz, 1H, NH—CH₂—CH₂), 7.68 and 7.63 (d, J=7.7 Hz, 1H, arom), 6.98-7.48 (m, 13H, arom), 4.61-4.69 (m, 1H, NH—CH), 3.98-4.02 (m, 1H, NH—CH₂—C₆H₄Cl), 3.75 (m, 1H, NH—CH—CH₃), 3.60-3.67 and 3.39-3.43 (m, 1H, NH—CH₂—C₆H₄Cl), 3.34-3.38 (m, 1H, NH—CH₂—CH₂), 3.24-3.29 (m, 1H, NH—CH₂—CH₂), 3.05-3.08 (m, 1H, NH—CH—CH₂), 2.85-2.92 (m, 1H, NH—CH—CH₂), 2.67-2.71 (m, 2H, NH—CH₂—CH₂), 1.33 and 1.10 (d, J=6.9 Hz, 3H, CH₃). HPLC-MS (ESI) m/z 291.2 (30), 308.1 (100), 503.2 (35) [M+H]⁺, 525.4 (15) [M+Na]⁺, 1027.1 (20) [2M+Na]⁺.

EXAMPLE 4

N1-phenethyl-(2R)-2-{N'-[2-(3-pyridyl)-ethanoyl]-hydrazino}-carboxamido-3-(1H-3-indolyl)-propanamide (181)

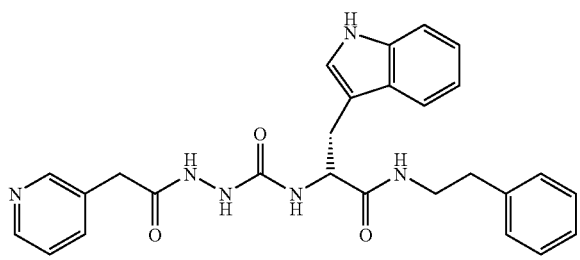

A) 10.0 g Boc-hydrazine was dissolved in 200 ml dry dichloromethane and 12.95 ml DIPEA (75.6 mmol) and the solution was then cooled to 0° C. A solution of 19.6 g FmocCl in 100 ml dry dichloromethane was added dropwise to this receiving solution over a period of 30 min. Then the reaction mixture was stirred overnight at RT. Following this, the organic phase was extracted with 200 ml water, dried over $Na_2SO_4$ and concentrated in a water pump vacuum to a volume of 100 ml. Then 100 ml trifluoroacetic acid was added with ice cooling and the mixture was stirred for 1.5 h. 300 ml saturated aqueous $Na_2CO_3$ solution was added to the mixture, the mixture was filtered and the separated organic phase was dried over $Na_2SO_4$. Evaporating the solvent in a water pump vacuum and drying the resulting residue in an oil pump vacuum yielded 18.02 g N-[(9H-fluoren-9-ylmethoxy)-carbonyl]-hydrazine (70.8 mmol) as colorless solid with a melting point of 150-153° C.

$^1$H-NMR (250 MHz, DMSO-$d_6$, 300 K) δ=10.10 (bs, 1H, NH), 9.60 (bs, 1H, NH), 7.89 (d, J=7.6 Hz, 2H, arom), 7.70 (d, J=7.3 Hz, 2H, arom), 7.30-7.45 (m, 4H, arom), 4.48 (d, J=6.6 Hz, 2H, CO—$CH_2$), 4.27 (t, J=6.7 Hz, 1H, CO—$CH_2$—CH).

B) A suspension of 1.49 g of the N-[(9H-fluoren-9-ylmethoxy)-carbonyl]-hydrazine obtained above (5.78 mmol), 60 ml dichloromethane and 60 ml saturated aqueous $NaHCO_3$ solution was stirred vigorously for 5 min. at 0° C. and then left to stand for 5 min. at this temperature. Then 7.95 ml of a 1.89 M phosgene solution in toluene was added to the bottom organic phase using a syringe. Once addition was complete, the reaction mixture was stirred vigorously for a further 10 min. Then 20 ml water and 20 ml dichloromethane were added to the reaction mixture and the phases were quickly separated. The aqueous phase was extracted with 50 ml dichloromethane and the combined organic phases were dried over $Na_2SO_4$. After evaporating off the solvent in a water pump vacuum and drying the residue in an oil pump vacuum, 1.35 g 5-(9H-fluoren-9-ylmethoxy)-3H-[1,3,4]oxadiazol-2-one (4.82 mmol) was obtained as colorless solid with a melting point of 125° C.

$^1$H-NMR (250 MHz, $CDCl_3$, 300 K) δ=8.72 (bs, 1H, NH), 7.77 (d, J=7.5 Hz, 2H, arom), 7.59 (d, J=7.4 Hz, 2H, arom), 7.28-7.45 (m, 4H, arom), 4.49 (d, J=7.8 Hz, 2H, $CH_2$—CH), 4.32-4.41 (m, 1H, $CH_2$—CH).

C) 100 mg of an FMPE resin laden with Fmoc-D-Trp(Boc)-phenylethylamide (for preparation see Example 1A); loading 0.354 mmol/g; corresponding to 22.3 mg (0.035 mmol) free Fmoc-D-Trp(Boc)-phenylethylamide) was allowed to swell for 10 min. in 5 ml NMP and then treated twice, each time for 15 min., with 5 ml each time of a freshly prepared 20%-strength (v/v) solution of piperidine in NMP. Following this, the resin was washed five times for three min. each time with 5 ml NMP each time, and once again five times each time for three min. with 5 ml dichloromethane each time. Then the resin was left to stand for 30 min. in 5 ml dry dichloromethane. After separation of the solvent by filtration, a solution of 30.5 mg of the 5-(9H-fluoren-9-ylmethoxy)-3H-[1,3,4]oxadiazol-2-one obtained above under B) in 1 ml dry dichloromethane was added to the FMPE resin laden with D-Trp(Boc)-phenylethylamide and the mixture was shaken for 90 min. Finally, the resin was washed five times for three min. with 5 ml dichloromethane each time and then another five times for three min. with 5 ml NMP each time. An FMPE resin laden with Fmoc-hydrazine-carbonyl-D-Trp(Boc)-phenylethylamide was obtained, which was used directly for the reaction below without isolating the intermediate product.

C) The entire amount of the laden FMPE resin obtained above [at assumed 100% conversion laden with 0.354 mmol/g Fmoc-hydrazine-carbonyl-D-Trp(Boc)-phenylethylamide, corresponding to 24 mg (0.035 mmol) of the free compound] was treated to cleave off the Fmoc protective group as described in Example 1B). An FMPE resin laden with hydrazine-carbonyl-D-Trp(Boc)-phenylethylamide was obtained, which was used directly for the reaction below without cleaving off and isolating the intermediate product.

D) The entire amount of the laden FMPE resin obtained above [at assumed 100% conversion laden with 0.354 mmol/g hydrazine-carbonyl-D-Trp(Boc)-phenylethylamide, corresponding to 16.5 mg (0.035 mmol) of the free compound] was washed five times for three min. with 5 ml NMP each time. Then a solution of 12 mg 3-pyridylacetic acid (0.07 mmol), 9.5 mg HOBT×$H_2O$ (0.07 mmol) and 22.5 mg TBTU (0.07 mmol) in 2 ml NMP was added to the laden FMPE resin. Finally 34 μl DIPEA (0.2 mmol) was added to the resulting receiving solution and the mixture was shaken for 45 min. Once the FMPE resin had been washed five times for three min. with 5 ml NMP each time, the coupling step described above was repeated. Finally it was washed another five times for three min. with 5 ml NMP each time. An FMPE resin laden with 3-pyridyl acetate-hydrazine-carbonyl-D-Trp(Boc)-phenylethylamide was obtained, which was used directly for the reaction below without isolating the intermediate product.

E) The entire amount of the laden FMPE resin obtained above [at assumed 100% conversion laden with 0.354 mmol/g 3-pyridyl acetate-hydrazine-carbonyl-D-Trp(Boc)-phenylethylamide, corresponding to 20.5 mg (0.035 mmol) of the free compound] was treated to cleave off the FMPE resin and remove the Boc protective group as described under Example 1G). After HPLC purification and freeze-drying, 4.5 mg (0.0093 mmol) of the title compound was obtained as colorless powder with a melting point of 116-120° C.

$^1$H-NMR (500 MHz, DMSO-$d_6$, 300 K) δ=10.79 (s, 1H, NH), 9.89 (s, 1H, NH), 8.63 (s, 1H, arom), 8.61 (d, J=5.0 Hz, 1H, arom), 8.02-8.04 (m, 2H, NH and arom), 7.96 (bs, 1H, NH—$CH_2$—$CH_2$), 7.63 (t, J=5.5 Hz, 1H, arom), 7.51 (d, J=7.9 Hz, 1H, arom), 7.30 (d, J=8.2 Hz, 1H, arom), 7.25 (t, J=7.6 Hz, 2H, arom), 6.99-7.18 (m, 5H, arom), 6.95 (t, J=8.0 Hz, 1H, arom), 6.44 (d, J=8.1 Hz, 1H, NH—CH), 4.32-4.36 (m, 1H, NH—CH), 3.59 (s, 2H, CO—$CH_2$—$C_5H_4N$), 3.22-

3.26 (m, 1H, NH—CH$_2$—CH$_2$), 3.15-3.19 (m, 1H, NH—CH$_2$—CH$_2$), 3.01 (dd, J=14.4 Hz, J=5.6 Hz, 1H, NH—CH—CH$_2$), 2.91 (dd, J=14.6 Hz, J=7.4 Hz, 1H, NH—CH—CH$_2$), 2.58 (t, J=7.5 Hz, 2H, NH—CH$_2$—CH$_2$). HPLC-MS (ESI) m/z 152.1 (40), 185.2 (30), 334.2 (30), 485.3 (100) [M+H]$^+$, 507.3 (70) [M+Na]$^+$, 523.3 (10) [M+Na]$^+$, 969.3 (20) [2M+H]$^+$, 991.4 (50) [2M+Na]$^+$, 1007.5 (20) [2M+K]$^+$.

EXAMPLE 5

N1-phenethyl-(2R)-2-[N'-(4-chlorobenzyl)-hydrazino]-carboxamido-3-(1H-3-indolyl)-propanamide (185)

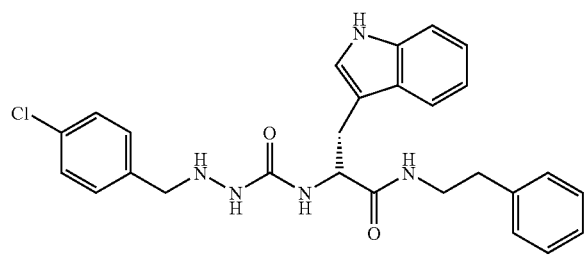

A) 2.12 g 4-chlorobenzaldehyde in 5 ml THF was added dropwise to a solution of 1.98 g tert-butyl carbazate (Boc-hydrazine) in 15 ml THF with constant stirring at room temperature over a period of 10 min. After 3 hours, the solvent was evaporated in a water pump vacuum and the resulting residue was purified by flash chromatography at a pressure of 1-1.2 bar (stationary phase: Silicagel 60, grain size 0.040-0.063 mm, mobile phase: ethyl acetate/hexane 1:5). After evaporating the solvent in a water pump vacuum and drying the residue in an oil pump vacuum, 3.64 g tert-butyl N'-(4-chlorophenylmethylene)-hydrazine-carboxylate was obtained as colorless solid with a melting point of 170-171° C.

MS (EI) m/z 41.2 (20), 57.2 (100), 154.0 (10), 181.0 (5), 197.9 (20), 253.9 (5) [M]$^+$.

B) 0.55 g NaCNBH$_3$ was added to a suspension of 1.5 g of the tert-butyl N'-(4-chlorophenylmethylene)-hydrazine-carboxylate obtained above in 25 ml dry THF with ice cooling and under argon protective gas atmosphere. 10 ml acetic acid was added dropwise to this mixture over a period of 10 min. The resulting clear solution was stirred overnight at RT. Then 60 ml water and 60 ml ethyl acetate were added and the pH value of the aqueous phase was set to 8 with NaHCO$_3$. The organic phase was separated and washed in succession with 50 ml saturated aqueous NaHCO$_3$ solution and with 50 ml saturated aqueous common salt solution. The organic phase was dried over Na$_2$SO$_4$ and the solvent was evaporated in a water pump vacuum. 40 ml methanol and 20 ml 1N NaOH were added to the remaining colorless residue in succession and the resulting mixture was first stirred for 1 hour at RT and then heated to boiling under reflux cooling for 1 hour. The mixture cooled to RT was extracted three times with diethyl ether, the combined ether phases were dried over Na$_2$SO$_4$ and the solvent was evaporated in a water pump vacuum. The remaining yellow oil was purified by flash chromatography at a pressure of 1-1.2 bar (stationary phase: Silicagel 60, grain size 0.040-0.063 mm, mobile phase: ethyl acetate/hexane 1:4). Evaporating the solvent in a water pump vacuum and drying the residue in an oil pump vacuum yielded 1.05 g N-(tert-butoxycarbonyl)-N'-(4-chlorobenzyl)-hydrazine as colorless solid with a melting point of 77-82° C.

$^1$H-NMR (250 MHz, DMSO-d$_6$,300 K) δ=8.23 (bs, 1H, NH—CO), 7.35 (m, 4H, arom), 4.84 (bs, 1H, NH—CH$_2$), 3.85 (s, 2H, NH—CH$_2$), 1.37 (s, 9H, CH$_3$).

C) 0.8 g of the N-(tert-butoxycarbonyl)-N'-(4-chlorobenzyl)-hydrazine obtained above was suspended with ice cooling in a mixture of 4 ml dioxane and 16 ml 10%-strength aqueous NaHCO$_3$ solution. Then a solution of 0.89 g FmocCl in 10 ml dioxane was added over a period of 10 min. and the reaction mixture was then stirred overnight at RT. 50 ml water was added and the aqueous phase was extracted three times with 100 ml diethyl ether each time. The organic phases which had been separated off were combined, dried over Na$_2$SO$_4$ and the solvent was finally evaporated in a water pump vacuum. The residue was purified by flash chromatography at a pressure of 1-1.2 bar (stationary phase: Silicagel 60, grain size 0.040-0.063 mm, mobile phase: ethyl acetate/hexane 1:2). Evaporating the solvent in a water pump vacuum and drying the residue in an oil pump vacuum yielded 1.37 g N-(4-chlorobenzyl)-N-[(9H-fluoren-9-ylmethoxy)-carbonyl]-N'-(tert-butoxycarbonyl)-hydrazine as colorless solid with a melting point of 53-55° C.

$^1$H-NMR (250 MHz, DMSO-d$_6$, 300 K) δ=9.62 (s, 1H, NH), 7.89 (d, J=7.3 Hz, 2H, arom), 7.74 (d, J=6.7 Hz, 1H, arom), 7.56 (m, 1H, arom), 7.27-7.43 (m, 7H, arom), 6.99 (m, 1H, arom), 4.2-5.52 (m, 5H, N—CH$_2$ and CO—CH$_2$—CH), 1.43 (s, 9H, CH$_3$).

D) 0.1 ml triisopropylsilane was added to a solution of 0.30 g of the N-(4-chlorobenzyl)-N-[(9H-fluoren-9-ylmethoxy)-carbonyl]-N'-(tert-butoxycarbonyl)-hydrazine obtained above under C) in 2.5 ml dichloromethane and the mixture was cooled to 0° C. Then 2.5 ml TFA was added dropwise over a period of 5 min. and the solution was then stirred for 30 min. The solvent was evaporated in a water pump vacuum with nitrogen cooling and the residue was taken up again in a solution of 77 mg DMAP (0.63 mmol) in 10 ml dry dichloromethane. This mixture was added dropwise and with stirring over a period of 20 min. to a solution of 0.25 g dipentafluorophenyl carbonate (0.63 mmol) in 20 ml dry dichloromethane. After complete addition, a solution of 0.26 g tert-butyl-3-[(2R)-2-amino-2-(phenethylcarbamoyl)-ethyl]-1H-1-indole carboxylate (for preparation see Example 3D)), 77 mg DMAP (0.63 mmol) and 10 ml dry dichloromethane was added to the receiving solution thus obtained, with stirring. It was stirred for 30 min. at RT, the solvent was evaporated in a water pump vacuum and the residue was taken up in 4 ml dichloromethane. Then 0.1 ml triisopropylsilane was added and the mixture cooled to 0° C. Then 4 ml TFA was added dropwise over a period of 5 min. and the mixture was then stirred for 30 min. The solvent was removed in an oil pump vacuum and 10 ml of a 20%-strength (v/v) solution of piperidine in DMF was added to the dried residue for 30 min. at RT. The solvent was evaporated in a water pump vacuum with nitrogen-cooled receiving solution, the remaining residue was taken up in DMSO and this was purified by reversed-phase HPLC [(HPLC system Amersham Pharmacia Biotech Äkta Basic 100 F; pump system P-900 and detector UV-900; column ODS-A C$_{18}$ from Omnicrom YMC (250 mm×20 mm, 10 µm, flow rate: 8 ml/min); elution with linear gradient (30 min.) of water (solvent A) in acetonitrile (solvent B) and 0.1% (v/v) TFA]. Freeze-drying the purified fractions yielded 26.8 mg of the title compound as colorless powder with a melting point of 75-80° C.

¹H-NMR (500 MHz, ACN-d₃, 300 K) δ=9.74 (bs, 1H, NH), 7.91 (d, J=7.7 Hz, 1H, arom), 7.98 (d, J=8.1 Hz, 1H, arom), 7.58-7.83 (m, 12H, arom), 6.99 (bs, 1H, NH—CH), 6.89 (bs, 1H, NH—CH₂—CH₂), 4.87 (q, J=6.9 Hz, NH—CH), 4.34 (bs, 2H, NH—CH₂—C₆H₄Cl), 3.87-3.94 (m, 1H, NH—CH₂—CH₂), 3.76-3.82 (m, 1H, NH—CH₂—CH₂), 3.66 (d, J=6.2 Hz, 2H, NH—CH—CH₂), 3.17 (t, J=7.3 Hz, 2H, NH—CH₂—CH₂). HPLC-MS (ESI) m/z 490.1 (70) [M+H]⁺, 512.3 (50) [m+Na]⁺, 754.8 (100), 978.9 (25) [2M+H]⁺, 1001.0 (90) [2M+Na]⁺, 1063.1 (20).

EXAMPLE 6

N1-phenethyl-(2R)-2-[N'-(furan-2-ylmethylene)-hydrazino]-carboxamido-3-(1H-3-indolyl)-propanamide (189)

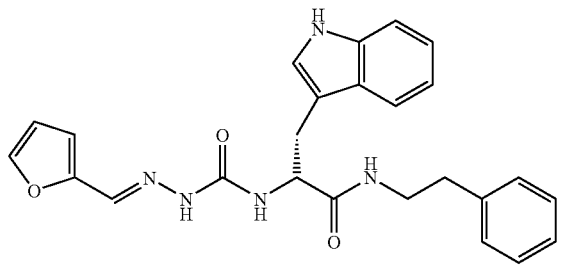

500 mg tert butyl-3-[(2R)-2-amino-2-(phenethylcarbamoyl)-ethyl]-1H-1-indole carboxylate (for preparation see Example 3D)) and 515 mg freshly prepared 5-(9H-fluoren-9-ylmethoxy)-3H-[1,3,4]oxadiazol-2-one (for preparation see Example 4B)) were dissolved in 20 ml dry DMF and stirred for 75 min. at RT. The solvent was then evaporated in a water pump vacuum with nitrogen-cooled receiving solution and the residue was purified by column chromatography (stationary phase: Silicagel 60, grain size 0.040-0.063 mm, mobile phase: chloroform/methanol, 20:1). The solvent was again evaporated in a water pump vacuum and the residue was dried in an oil pump vacuum. 0.58 g N1-phenethyl-(2R)-2-{[N'-(9H-fluoren-9-ylmethoxy)-carbonyl]-hydrazino}-carboxamido-3-[1-tert-butoxycarbonyl)-3-indolyl]-propanamide (=Fmoc-hydrazine-carbonyl-D-Trp(Boc)-phenylethylamide) was obtained as colorless solid with a melting point of 135-137° C.

HPLC-MS (ESI) m/z 179.2 (10), 334.3 (10), 378.2 (10), 588.4 (10), 632.3 (25), 654.4 (35), 688.3 (80) [M+H]⁺, 710.4 (100) [M+Na]⁺, 1375.5 (40) [2M+H]⁺, 1397.5 (25) [2M+Na]⁺.

A) 179 mg of the Fmoc-hydrazine-carbonyl-D-Trp(Boc)-phenylethylamide obtained above was dissolved in 2 ml of a 20%-strength (v/v) solution of piperidine in DMF and stirred for 30 min. at RT. Then the solvent was evaporated in a water pump vacuum with nitrogen-cooled receiving solution and the residue was taken up in 10 ml THF. 25 mg furan-2-carbaldehyde was added to this receiving solution and the mixture was stirred for 24 hours at RT. Then a further 50 mg furan-2-carbaldehyde was added and the mixture was stirred for another 24 hours. The solvent was evaporated in a water pump vacuum and the residue was purified by flash chromatography at a pressure of 1-1.2 bar (stationary phase: Silicagel 60, grain size 0.040-0.063 mm, mobile phase: ethyl acetate/hexane 1:1).

After evaporating the solvent in a water pump vacuum and drying the residue in an oil pump vacuum, 100 mg N1-phenethyl-(2R)-2-[N'-(furan-2-ylmethylene)-hydrazino]-carboxamido-3-[1-(tert-butoxycarbonyl)-3-indolyl]-propanamide was obtained as colorless, crystalline solid.

MS (ESI) m/z 510.3 (15), 544.3 (55) [M+H]⁺, 566.3 (50) [M+Na]⁺, 835.2 (25) [(3M+K+H)/2]²⁺, 1087.4 (45) [2M+H]⁺, 1109.5 (100) [2M+Na]⁺, 1630.3 (5) [3M+H]⁺, 1652.2 (20) [3M+Na]⁺.

B) 100 mg of the Ni-phenethyl-(2R)-2-[N'-(furan-2-ylmethylene)-hydrazino]-carboxamido-3-[1-(tert-butoxycarbonyl)-3-indolyl]-propanamide obtained above was dissolved in 3 ml dichloromethane. 0.1 ml triisopropylsilane was added thereto and the mixture was then cooled to 0° C. Then 3 ml TFA was added dropwise over a period of 5 min. and the reaction mixture was stirred for 1 hour. Then the solvent was evaporated in a water pump vacuum, the remaining residue was taken up in a mixture of 8 ml DMSO, 1 ml water and 1 ml acetic acid, and was stirred overnight at RT. Then the solvent was evaporated to dryness in a water pump vacuum with nitrogen-cooled receiving solution and the residue was taken up in DMSO. Reversed-phase HPLC [HPLC system Amersham Pharmacia Biotech Akta Basic 100F; pump system P-900 and detector UV-900; column ODS-A C₁₈ from Omnicrom YMC (250 mm×20 mm, 10 µm, flow rate: 8 ml/min); elution with linear gradient (30 min.) of water (solvent A) in acetonitrile (solvent B) and 0.1% (v/v) TFA and freeze-drying of the purified fractions yielded 46 mg of the title compound as colorless powder with a melting point of 100-101° C.

¹H-NMR (500 MHz, DMSO-d₆, 300 K) δ=10.82 (s, 1H, NH—CH—C), 10.41 (s, 1H, N—NH), 8.09 (t, J=5.5 Hz, 1H, NH—CH₂), 7.75 (s, 1H, arom), 7.73 (s, 1H, arom), 7.55 (d, J=7.9 Hz, 1H, arom), 7.30 (d, J=8.1 Hz, 1H, arom), 7.23-7.26 (m, 2H, arom), 7.14-7.17 (m, 3H, arom), 7.07 (s, 1H, arom), 7.03 (t, J=7.4 Hz, 1H, arom), 6.93 (t, J=7.5 Hz, 1H, arom), 6.74 (d, J=3.2 Hz, 1H, arom), 6.58-6.60 (m, 2H, NH—CH—CH₂ and arom), 4.45 (q, J=6.8 Hz, 1H, NH—CH), 3.24-3.31 (m, 1H, NH—CH₂), 3.17-3.24 (m, 1H, NH—CH₂), 3.02-3.10 (m, 2H, NH—CH—CH₂), 2.62 (t, J=7.4 Hz, 2H, NH—CH₂—CH₂). HPLC-MS (ESI) m/z 444.2 (30) [M+H]⁺, 466.3 (65) [M+Na]⁺, 685.1 (90), 909.2 (100) [2M+Na]⁺, 1352.1 (15) [3M+Na]⁺.

EXAMPLE 7

N1-phenethyl-(2R)-2-[(4-benzylpiperidino)-methyl]-carboxamido-3-(1H-3-indolyl)-propanamide

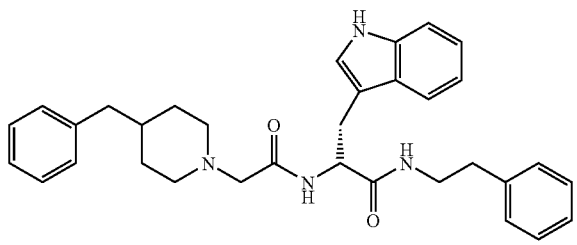

A) 3.0 g 4-benzylpiperidine and 1.73 g triethylamine was added dropwise to 13 ml toluene with stirring and ice cooling. A solution of 2.86 g ethyl bromoacetate in 6.2 ml toluene was added dropwise to this receiving solution over a period of 4 h. Following this the reaction mixture was stirred for 4 days at RT. Then the organic phase was extracted with 100 ml water and then dried over $Na_2SO_4$. The solvent was evaporated in a water pump vacuum and the residue was dried in an oil pump vacuum. 4.02 g ethyl (4-benzyl-piperidin-1-yl) acetate was obtained as colorless oil.

HPLC-MS (ESI) m/z 188.2 (100), 234.2 (45), 262.2 (100) [M+H]$^+$.

B) 1.0 g of the ethyl (4-benzyl-piperidin-1-yl) acetate obtained above was added to a receiving solution consisting of 5.755 ml 1N aqueous NaOH and 11.5 ml methanol. It was stirred overnight at RT, then neutralized with conc. hydrochloric acid and the solvent was evaporated in a water pump vacuum. The residue was purified by flash chromatography at a pressure of 1-1.2 bar (stationary phase: Silicagel 60, grain size 0.040-0.063 mm, mobile phase: methanol/chloroform 1:1). After evaporating the solvent in a water pump vacuum and drying the residue in an oil pump vacuum, 0.89 g (4-benzyl-piperidin-1-yl)-acetic acid was obtained as a colorless solid with a melting point of 250-252° C.

GC-MS (EI) m/z 44.1 (10), 91.1 (15), 188.1 (100), 233.0 (5) [M]$^+$.

C) 86 mg of the (4-benzyl-piperidin-1-yl)-acetic acid obtained above under B), 150 mg tert butyl-3-[(2R)-2-amino-2-(phenethylcarbamoyl)-ethyl]-1H-1-indole carboxylate (for preparation see Example 3D)), 75 mg HOBT and 177 mg TBTU were dissolved in 2.6 ml DMF. 0.20 g DIPEA was added dropwise to this receiving solution over a period of 5 min. Then the reaction mixture was stirred for 23 h, the solvent was evaporated in a water pump vacuum with nitrogen-cooled receiving solution and the remaining residue was purified by flash chromatography at a pressure of 1-1.2 bar (stationary phase: Silicagel 60, grain size 0.040-0.063 mm, mobile phase: chloroform/methanol, 10:1). 180 mg N1-phenethyl-(2R)-2-[(-benzylpiperidino)-methyl]-carboxamido-3-[1-(tert-butoxycarbonyl)-3-indolyl]-propanamide was obtained as yellow oil.

HPLC-MS (ESI) m/z 188.1 (20), 567.3 (70), 623.3 (100) [M+H]$^+$, 645.2 (25) [M+Na]$^+$, 1245.2 (10) [2M+H]$^+$, 1267.3 (40) [2M+Na]$^+$.

D) 180 mg of the N1-phenethyl-(2R)-2-[(4-benzylpiperidino)-methyl]-carboxamido-3-[1-(tert-butoxycarbonyl)-3-indolyl]-propanamide obtained above was dissolved in 3 ml dichloromethane. 0.1 ml triisopropylsilane was added thereto and the solution was cooled to 0° C. Then 3 ml TFA was added dropwise over a period of 5 min. and the reaction mixture was stirred for 1 hour. Following this the solvent was evaporated in a water pump vacuum with nitrogen-cooled receiving solution. The remaining residue was taken up in a mixture of 8 ml DMSO, 1 ml water and 1 ml acetic acid and stirred overnight. Then the solvent was evaporated to dryness in a water pump vacuum with nitrogen-cooled receiving solution. The residue was taken up in DMSO and purified by reversed-phase HPLC [HPLC system from *Amersham Pharmacia Biotech* Äkta Basic 100F; pump system P-900 and detector UV-900; column ODS-A $C_{18}$ from *Omnicrom YMC* (250 mm×30 mm, 10 μm, flow rate: 25 ml/min); elution with linear gradient (30 min.) of water (solvent A) in acetonitrile (solvent B) and 0.1% (v/v) TFA]. Freeze-drying the purified fractions yielded 109 mg of the title compound as colorless powder with a melting point of 73-75° C.

$^1$H-NMR (500 MHz, DMSO-d$_6$, 300 K) δ=10.84 (s, 1H, NH—CH—C), 8.81 (d, J=8.3 Hz, 1H, NH—CH), 8.25 (t, J=5.2 Hz, NH—CH$_2$—CH$_2$), 7.61 (d, J=7.7 Hz, 1H, arom), 7.07-7.33 (m, 12H, arom), 7.02 (t, J=7.3 Hz, 1H, arom), 6.96 (t, J=6.9 Hz, 1H, arom), 4.60 (q, J=6.9 Hz, 1H, NH—CH), 3.81 (d, J=15.2 Hz, 1H, N—CH$_2$—CO), 3.67 (d, J=13.1 Hz, 1H, N—CH$_2$—CO), 3.21-3.34 (m, 3H, NH—CH$_2$—CH$_2$ and N—CH$_2$—CH$_2$—CH), 3.06 (dd, J=14.4 Hz, J=4.9 Hz, 1H, NH—CH—CH$_2$), 2.97-2.93 (m, 3H, NH—CH—CH$_2$ and N—CH$_2$—CH$_2$—CH), 2.59-2.67 (m, 3H, NH—CH$_2$—CH$_2$ and N—CH$_2$—CH$_2$—CH), 2.46-2.48 (m, 2H, CH—CH$_2$—C$_6$H$_5$), 1.57-1.70 (m, 3H, N—CH$_2$—CH$_2$—CH and CH), 1.32-1.46 (m, 2H, NCH$_2$—CH$_2$—CH). HPLC-MS (ESI) m/z 188.1 (70), 523.3 (100) [M+H]$^+$, 803.7 (20), 1045.1 (20) [2M+H]$^+$, 1067.3 (40) [2M+Na]$^+$.

The compounds of Formula I listed in the following Table 2 can also be prepared according to the preparation processes described above or analogously to these preparation processes. Table 2 contains the following abbreviations:

| | |
|---|---|
| bo: | bond |
| dm: | dioxolanylmethyl |
| Ind: | indolyl |
| Phe: | phenyl |
| Py: | pyridyl |
| rac.: | racemic |
| THI: | tetrahydroisoquinolyl |

TABLE 2

Further compounds of Formula I

| Ex. No | A$^1$ | A$^2$ | A$^3$ | R$^1$ | R$^2$ | R$^3$ | Ar$^1$ | Ar$^2$ | Ar$^3$ | m | n | (HR)MS m/z |
|---|---|---|---|---|---|---|---|---|---|---|---|---|
| 8 | (R)—CH— | C(O) | (S)—CH—[(CH$_2$)$_2$(CO)NH$_2$] | —NH$_2$ | H | H | Phe | 3-Ind | Phe | 1 | 0 | |
| 9 | (R)—CH— | C(O) | (S)—CH—[(CH$_2$)$_2$(CO)NH$_2$] | —NH$_2$ | H | H | Phe | 3-Ind | 4-Br-Phe | 1 | 1 | |
| 10 | (R)—CH— | C(O) | (S)—CH—[(CH$_2$)$_2$(CO)NH$_2$] | —NH$_2$ | H | H | Phe | 3-Ind | 2-Py | 1 | 1 | |
| 11 | (R)—CH— | C(O) | (S)—CH—[(CH$_2$)$_2$(CO)NH$_2$] | —NH$_2$ | H | (R)—CH$_3$ | Phe | 3-Ind | Phe | 1 | 1 | |
| 12 | (R)—CH— | C(O) | (S)—CH—[(CH$_2$)$_2$(CO)NH$_2$] | —NH$_2$ | H | (S)—CH$_3$ | Phe | 3-Ind | Phe | 1 | 1 | |
| 13 | —CH— | C(O) | (S)—CH—[(CH$_2$)$_2$(CO)NH$_2$] | H | H | H | 1-THI (rac) | 3-Ind | Phe | 0 | 1 | 609.32 |
| 14 | —CH— | C(O) | (S)—CH—[(CH$_2$)$_2$(CO)NH$_2$] | H | H | H | 4-Cl-Phe | 3-Ind | Phe | 1 | 1 | 602.25 |
| 15 | —CH— | C(O) | (S)—CH—[(CH$_2$)$_2$(CO)NH$_2$] | H | H | H | 2-Ind | 3-Ind | Phe | 0 | 1 | 593.29 |
| 16 | —CH— | C(O) | (S)—CHCH$_3$ | H | H | H | 4-Cl-Phe | 3-Ind | Phe | 0 | 1 | 531.21 |
| 17 | —CH— | C(O) | (S)—CHCH$_3$ | H | H | H | 1-THI (rac) | 3-Ind | Phe | 0 | 1 | 552.30 |
| 18 | —CH— | C(O) | (S)—CHCH$_3$ | H | H | H | 3,4-dm-Phe | 3-Ind | Phe | 0 | 1 | 541.25 |
| 19 | —CH— | C(O) | (S)—CHCH$_3$ | H | H | H | 3-Py | 3-Ind | Phe | 0 | 1 | 498.25 |
| 20 | —CH— | C(O) | (S)—CHCH$_3$ | H | H | H | 2-Ind | 3-Ind | Phe | 0 | 1 | 536.27 |

TABLE 2-continued

Further compounds of Formula I

| Ex. No | $A^1$ | $A^2$ | $A^3$ | $R^1$ | $R^2$ | $R^3$ | $Ar^1$ | $Ar^2$ | $Ar^3$ | m | n | (HR)MS m/z |
|---|---|---|---|---|---|---|---|---|---|---|---|---|
| 21 | —CH— | bo | —CH$_2$— | H | H | H | Phe | 3-Ind | Phe | 0 | 1 | 455.24 |
| 22 | —CH— | bo | —CH$_2$— | H | H | H | 4-Cl-Phe | 3-Ind | Phe | 0 | 1 | 489.21 |
| 23 | —CH— | bo | —CH$_2$— | H | H | H | 3-Py | 3-Ind | Phe | 0 | 1 | 456.24 |
| 24 | —CH— | bo | —CH$_2$— | H | H | H | Phe | 3-Ind | Phe | 1 | 1 | 469.26 |
| 25 | —CH— | bo | (S)—CHCH$_3$ | H | H | H | Phe | 3-Ind | Phe | 0 | 1 | 469.26 |
| 26 | —CH— | bo | (S)—CHCH$_3$ | H | H | H | Phe | 3-Ind | Phe | 1 | 1 | 483.28 |
| 27 | —CH— | C(O) | —NH— | H | H | H | Phe | 3-Ind | Phe | 0 | 1 | 484.23 |
| 28 | —CH— | C(O) | —NH— | H | H | H | 4-Cl-Phe | 3-Ind | Phe | 0 | 1 | 518.19 |
| 29 | —CH— | C(O) | —NH— | H | H | H | 1-THI (rac.) | 3-Ind | Phe | 0 | 1 | 539.28 |
| 30 | —CH— | C(O) | —NH— | H | H | H | 2-Ind | 3-Ind | Phe | 0 | 1 | 523.24 |
| 31 | —CH— | bo | —NH— | H | H | H | Phe | 3-Ind | Phe | 0 | 1 | 456.24 |
| 32 | —CH— | bo | —NH— | H | H | H | 2-furyl | 3-Ind | Phe | 0 | 1 | 446.22 |
| 33 | —CH— | bo | —NH— |  | bo | H | Phe | 3-Ind | Phe | 0 | 1 | 454.22 |
| 34 | —N— | —(CH$_2$)$_2$— | —CH$_2$— |  | —(CH$_2$)$_2$— | H | Phe | 3-Ind | Phe | 1 | 1 | 524.30 |

EXAMPLE I

Capsules Containing N1-phenethyl-(2R)-2-{1-[(4-chlorobenzyl)-amino]-ethylcarboxamido}-3-(1H-3-indolyl)-propanamide Capsules with the following composition per capsule were produced:

| | |
|---|---|
| N1-phenethyl-(2R)-2-{1-[(4-chlorobenzyl)-amino]-ethylcarboxamido}-3-(1H-3-indolyl)-propanamide | 20 mg |
| Corn starch | 60 mg |
| Lactose | 300 mg |
| Ethyl acetate | q.s. |

The active substance, the corn starch and the lactose were processed into a homogenous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg | and then filled into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to the Formula I

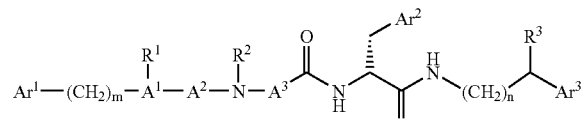

I wherein
$A^1$ is CH, or if $A^2$ is not a bond and $A^3$ is not NH, then $A^1$ may be nitrogen;
$A^2$ is a bond or $C_{1-2}$-alkylene, or if $A^1$ is CH and $R^2$ is hydrogen, then $A^2$ may be carbonyl;
$A^3$ is methylene which is optionally substituted by $C_{1-4}$-alkyl or $C_{1-4}$-alkylcarbonylamide, or if $R^2$ is hydrogen or together with $R^1$ represents a bond, then $A^3$ may be NH;
$R^1$ is hydrogen, or if $A^2$ is carbonyl, then $R^1$ may be amino, and
$R^2$ is hydrogen, or
$R^1$ and $R^2$ together may represent a bond if $A^2$ is a bond;
$R^3$ is hydrogen or methyl;
$Ar^1$ is phenyl which is optionally substituted 1 or 2 times by halogen or $C_{1-4}$-alkyl or by $C_{1-2}$-alkylenedioxy bonded to two adjacent ring carbon atoms, or is pyridyl, furyl, indolyl or tetrahydroisoquinolyl;
$Ar^2$ is furyl, benzofuranyl, thienyl, benzothiophenyl, pyrrolyl or indolyl;
$Ar^3$ is phenyl which is optionally substituted 1 or 2 times by halogen, or is pyridyl;
m is 0 or 1, and
n is 0 or 1;
or a physiologically acceptable acid addition salt thereof.

2. A compound corresponding to Formula I according to claim 1, wherein n is 1, and $R^3$ is hydrogen.

3. A compound corresponding to Formula I according to claim 1, wherein $Ar^2$ represents indolyl or benzothiophenyl.

4. A compound corresponding to Formula Ia

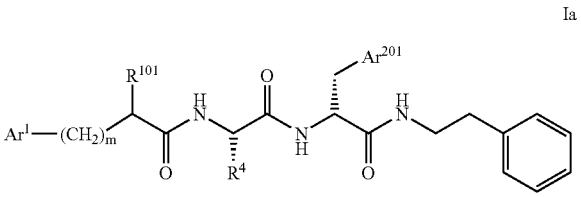

Ia wherein
$R^{101}$ is hydrogen or amino,
$R^4$ is hydrogen, $C_{1-4}$-alkyl or $C_{1-4}$-alkyl carbonylamide,
$Ar^1$ is phenyl which is optionally substituted 1 to 2 times by halogen or $C_{1-4}$-alkyl or by $C_{1-2}$-alkylenedioxy bonded to two adjacent ring carbon atoms; or is pyridyl, furyl, indolyl or tetrahydroisoquinolyl, Ar$^{201}$ is benzothiophenyl or indolyl, and m is 0 or 1 or a physiologically acceptable salt thereof.

5. A compound corresponding to Formula Ib

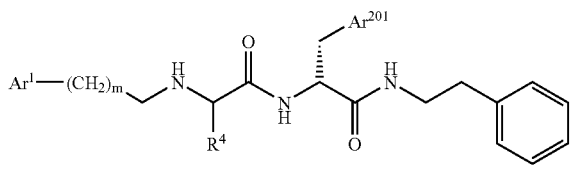

wherein

R$^4$ is hydrogen, C$_{1-4}$-alkyl or C$_{1-4}$-alkyl carbonylamide,

Ar$^1$ is phenyl which is optionally substituted 1 to 2 times by halogen or C$_{1-4}$-alkyl or by C$_{1-2}$-alkylenedioxy bonded to two adjacent ring carbon atoms; or is pyridyl, furyl, indolyl or tetrahydroisoquinolyl, Ar$^{201}$ is benzothiophenyl or indolyl, and m is 0 or 1, or a physiologically acceptable salt thereof.

6. A compound corresponding to Formula Ic

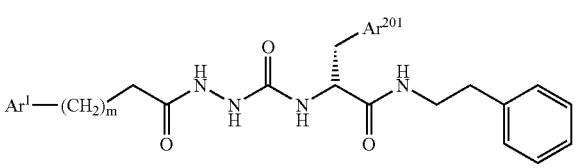

wherein

Ar$^1$ is phenyl which is optionally substituted 1 to 2 times by halogen or C$_{1-4}$-alkyl or by C$_{1-2}$-alkylenedioxy bonded to two adjacent ring carbon atoms; or is pyridyl, furyl, indolyl or tetrahydroisoquinolyl, Ar$^{201}$ is benzothiophenyl or indolyl, and m is 0 or 1, or a physiologically acceptable salt thereof.

7. A compound corresponding to Formula Id

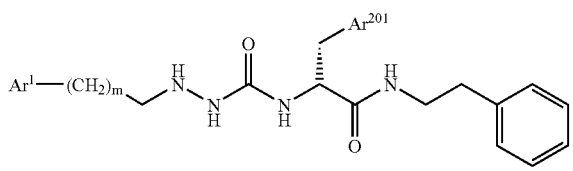

wherein

Ar$^1$ is phenyl which is optionally substituted 1 to 2 times by halogen or C$_{1-4}$-alkyl or by C$_{1-2}$-alkylenedioxy bonded to two adjacent ring carbon atoms; or is pyridyl, furyl, indolyl or tetrahydroisoquinolyl, Ar$^{201}$ is benzothiophenyl or indolyl, and m is 0 or 1, or a physiologically acceptable salt thereof.

8. A compound corresponding to Formula Ie

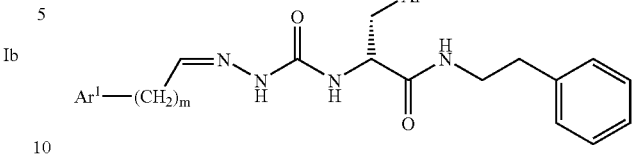

wherein

Ar$^1$ is phenyl which is optionally substituted 1 to 2 times by halogen or C$_{1-4}$-alkyl or by C$_{1-2}$-alkylenedioxy bonded to two adjacent ring carbon atoms; or is pyridyl, furyl, indolyl or tetrahydroisoquinolyl, Ar$^{201}$ is benzothiophenyl or indolyl, and m is 0 or 1, or a physiologically acceptable salt thereof.

9. A pharmaceutical composition comprising at least one compound corresponding to Formula I according to claim 1, and at least one pharmaceutical auxiliary or excipient.

10. A method of treating a condition selected from the group consisting of obesity, diabetes, and eating disorders, said method comprising administering to a patient in need thereof a pharmaceutically effective amount of a compound corresponding to Formula I according to claim 1.

11. A process for preparing a compound corresponding to formula I,

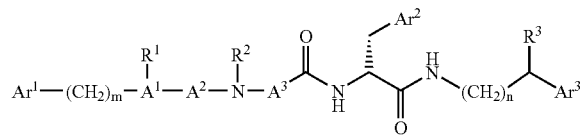

or a pharmaceutically acceptable salt thereof, wherein

A$^1$ is CH, or if A$^2$ is not a bond and A$^3$ is not NH, then A$^1$ may be nitrogen;

A$^2$ is a bond or C$_{1-2}$-alkylene, or if A$^1$ is CH and R$^2$ is hydrogen, then A$^2$ may be carbonyl;

A$^3$ is methylene which is optionally substituted by C$_{1-4}$-alkyl or C$_{1-4}$-alkylcarbonylamide, or if R$^2$ is hydrogen or together with R$^1$ represents a bond, then A$^3$ may be NH;

R$^1$ is hydrogen or, if A$^2$ is carbonyl, then R$^1$ may be amino, and

R$^2$ is hydrogen, or

R$^1$ and R$^2$ together may represent a bond if A$^2$ is a bond,

R$^3$ is hydrogen or methyl,

Ar$^1$ is phenyl which is optionally substituted 1 or 2 times by halogen or C$_{1-4}$-alkyl or by C$_{1-2}$-alkylenedioxy bonded to two adjacent ring carbon atoms, or is pyridyl, furyl, indolyl or tetrahydroisoquinolyl;

Ar$^2$ is furyl, benzofuranyl, thienyl, benzothiophenyl, pyrrolyl or indolyl;

Ar$^3$ is phenyl which is optionally substituted 1 or 2 times by halogen, or pyridyl;

m is 0 or 1 and n is 0 or 1, wherein
a) for the preparation of a compound of formula Ig

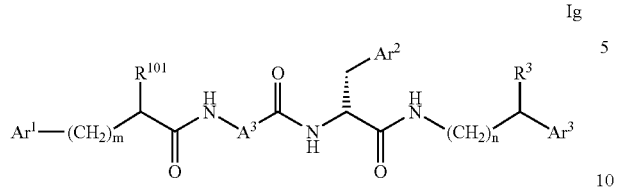

Ig wherein $A^3$, $R^3$, $Ar^1$, $Ar^2$, $Ar^3$, m and n have the above meanings and $R^{101}$ is hydrogen or amino, a compound of formula II

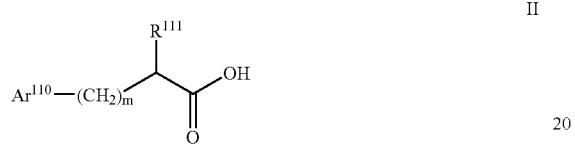

II wherein m has the above meaning, $Ar^{110}$ has the meaning given above for $Ar^1$, any reactive groups being protected by protective groups, and $R^{111}$ has the meaning given above for $R^{101}$, any amino group being protected by a protective group, is reacted with a compound of formula III

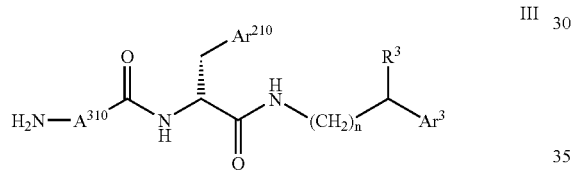

III wherein $R^3$, $Ar^3$ and n have the above meanings, $Ar^{210}$ has the meaning given above for $Ar^2$, any reactive groups being protected by protective groups, and $A^{310}$ has the meaning given above for $A^3$, any reactive nitrogen atoms being protected by protective groups, or b) for the preparation of a compound of formula Ih

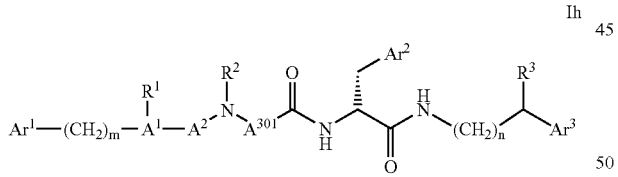

Ih wherein $A^1$, $A^2$, $R^1$, $R^2$, $R^3$, $Ar^1$, $Ar^2$, $Ar^3$, m and n have the above meanings and $A^{301}$ has the meaning given above for $A^3$ with the exception of NH, a compound of formula IV

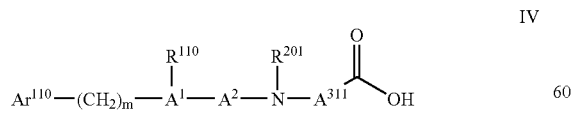

IV wherein $A^1$, $A^2$, $Ar^{110}$ and m have the above meanings, $A^{311}$ has the meaning given above for $A^{301}$, any reactive nitrogen atoms being protected by protective groups, $R^{110}$ has the meaning given above for $R^1$, any amino group being protected by a protective group, and $R^{201}$ has the meaning given above for $R^2$ with the exception of hydrogen, or an amino protective group, is reacted with a compound of formula V

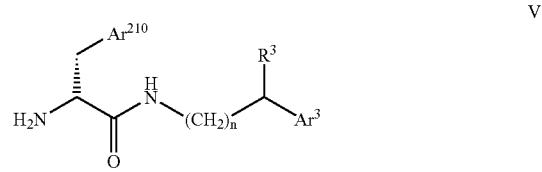

V wherein $R^3$, $Ar^{210}$, $Ar^3$ and n have the above meanings, or c) for the preparation of a compound of formula Ii,

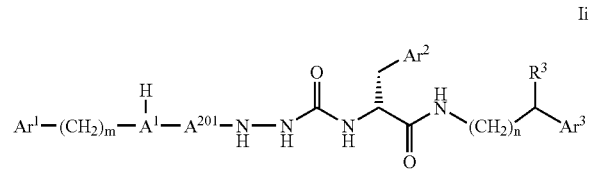

Ii wherein $A^1$, $R^3$, $Ar^1$, $Ar^2$, $Ar^3$, m and n have the above meanings and $A^{201}$ has the meaning given above for $A^2$ with the exception of carbonyl, a compound of Formula V is reacted with a carbonyl-group synthesis equivalent and with a compound of formula VI

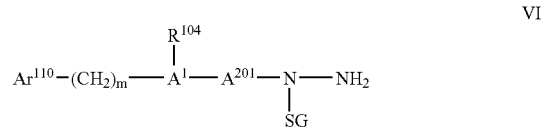

VI wherein $A^1$, $A^{201}$, $Ar^{110}$ and m have the above meanings, $R^{104}$ represents hydrogen or, if $A^1$ is nitrogen, then $R^{104}$ may be a nitrogen protective group, and SG represents a protective group suitable in peptide chemistry, or d) for the preparation of a compound of formula Ij

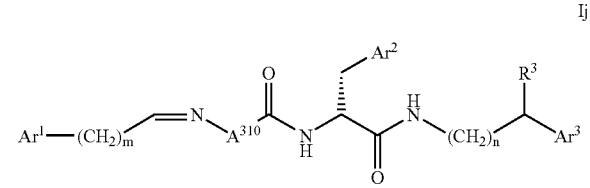

Ij wherein $A^{310}$, $R^3$, $Ar^1$, $Ar^2$, $Ar^3$, m and n have the above meanings, a compound of Formula III is reacted with a compound of formula VIII

VIII wherein $Ar^{110}$ and m have the above meanings;
and any protective groups are each subsequently cleaved off again;
and optionally converting a resulting compound of Formula I into a corresponding acid addition salt or optionally converting a resulting salt into a free compound of Formula I.

* * * * *